US011596688B2

(12) United States Patent
Rosario et al.

(10) Patent No.: US 11,596,688 B2
(45) Date of Patent: Mar. 7, 2023

(54) PREDICTING OUTCOME OF TREATMENT WITH AN ANTI-α4β7 INTEGRIN ANTIBODY

(71) Applicant: Millennium Pharmaceuticals, Inc., Cambridge, MA (US)

(72) Inventors: Maria Rosario, Mystic, CT (US); Timothy L. Wyant, Bellingham, MA (US); Brihad Abhyankar, Watford (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/455,103

(22) Filed: Jun. 27, 2019

(65) Prior Publication Data

US 2020/0155673 A1 May 21, 2020

Related U.S. Application Data

(63) Continuation of application No. 15/538,869, filed as application No. PCT/US2015/000476 on Dec. 23, 2015, now abandoned.

(60) Provisional application No. 62/096,636, filed on Dec. 24, 2014, provisional application No. 62/117,750, filed on Feb. 18, 2015, provisional application No. 62/132,917, filed on Mar. 13, 2015.

(51) Int. Cl.
| | |
|---|---|
| *A61K 39/00* | (2006.01) |
| *A61K 39/395* | (2006.01) |
| *G01N 33/53* | (2006.01) |
| *G01N 33/68* | (2006.01) |
| *C07K 16/28* | (2006.01) |

(52) U.S. Cl.
CPC ........ *A61K 39/395* (2013.01); *C07K 16/2839* (2013.01); *G01N 33/6854* (2013.01); *A61K 2039/505* (2013.01); *A61K 2039/54* (2013.01); *C07K 2317/24* (2013.01); *C07K 2317/94* (2013.01); *C12Q 2600/106* (2013.01); *C12Q 2600/158* (2013.01); *G01N 2333/52* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,147,851 B1 | 12/2006 | Ponath et al. | |
| 7,402,410 B2 | 7/2008 | Ponath et al. | |
| 9,663,579 B2 | 5/2017 | Fox et al. | |
| 9,764,033 B2 | 9/2017 | Diluzio et al. | |
| 10,004,808 B2 | 6/2018 | Fox et al. | |
| 10,040,855 B2 | 8/2018 | Diluzio et al. | |
| 10,143,752 B2 | 12/2018 | Fox et al. | |
| 2012/0282249 A1 | 11/2012 | Irving et al. | |
| 2014/0120084 A1 | 5/2014 | Anand et al. | |

FOREIGN PATENT DOCUMENTS

| | | |
|---|---|---|
| WO | 1996/024673 A1 | 8/1996 |
| WO | 1998/06248 A2 | 2/1998 |
| WO | 2001/078779 A2 | 10/2001 |
| WO | 2007/061679 A1 | 5/2007 |
| WO | 2012135589 A1 | 10/2012 |
| WO | 2012/151247 A2 | 11/2012 |
| WO | 2012/151248 A2 | 11/2012 |
| WO | 2016/086147 A1 | 6/2016 |

OTHER PUBLICATIONS

Sandborn et al. Vedolizumab as Induction and Maintenance Therapy for Crohn's Disease, n engl j med 369;8: 711-721, Aug. 2013) (Year: 2013).*
TGA, Extract from the Clinical Evaluation Report for Vedolizumab (rch). AusPAR attachment 2—Feb. 12, 2014. pp. 1-65. (Year: 2014).*
Rosario et al. Relationship between Vedolizumab Pharmacokinetics and Endoscopic outcomes of Patients With Ulcerative Colitis. Advances in Inflammatory Bowel Diseases, Dec. 4-6, 2014; Abstract 0-003. (Year: 2014).*
Feagan et al. Vedolizumab as Induction and Maintenance Therapy for Ulcerative Colitis. (N Engl. J Med, 369(8):699-710, 2013 including supplement pp. 1-47. (Year: 2013).*
NCT00783718. Study of Vedolizumab (MLN0002) in Patients With Moderate to Severe Ulcerative Colitis (Gemini I). Jul. 18, 2014 (Year: 2014).*
Ferrante et al. Validation of Endoscopic Activity Scores in Patients With Crohn's Disease Based on a Post Hoc Analysis of Data From SONIC. Gastroenterology, Nov. 2013, 145(5) pp. 978-986. (Year: 2013).*
Björkesten et al. Surrogate markers and clinical indices, alone or combined, as indicators for endoscopic remission in anti-TNF-treated luminal Crohn's disease. Scandinavian Journal of Gastroenterology. 2012; 47: 528-537. (Year: 2012).*
Ordas et al. Anti-TNF Monoclonal Antibodies in Inflammatory Bowel Disease: Pharmacokinetics-Based Dosing Paradigms. Clinical Pharmacology & Therapeutics | vol. 91 No. 4 | Apr. 2012 . pp. 635-646 (Year: 2012).*
Rosario et al. Population pharmacokinetics-pharmacodynamics of vedolizumab in patients with ulcerative colitis and Crohn's disease. Aliment Pharmacol Ther 2015; 42: 188-202 (Year: 2015).*
Dirks and Meibohm. Population Pharmacokinetics of Therapeutic Monoclonal antibodies. Clin Pharmacokinet. Oct. 2010;49(10):633-59. (Year: 2010).*
International Search Report and Written Opinion for Application No. PCT/US2015/000476, dated Jun. 30, 2016.

(Continued)

*Primary Examiner* — Maher M Haddad
(74) *Attorney, Agent, or Firm* — Womble Bond Dickinson (US) LLP

(57) ABSTRACT

The invention provides methods for treating patients with anti-α4β7 antibody comprising predicting outcome of the antibody therapy. The invention relates to the identification of patients who can respond to therapy comprising an anti-α4β7 antibody.

8 Claims, 16 Drawing Sheets

Specification includes a Sequence Listing.

(56) References Cited

OTHER PUBLICATIONS

Feagan, et al., "Vedolizuman as Induction and Maintenance Therapy for Ulcerative Colitis," The New England Journal of Medicine (Aug. 22, 2013), v. 369, No. 8, pp. 699-710.
Ordas, et al., "Accuracy of Magnetic Resonance Enterography in Assessing Response to Therapy and Mucosal Healing in Patients with Crohn's Disease," Gastroenterology (Feb. 2014), v. 146, No. 2, pp. 374-382.
Poole, et al., "Vedolizumab: First Global Approval," Drugs (Jul. 2, 2014), v. 74, pp. 1293-1303.
Center for Drug Evaluation and Research, Clinical Pharmacology and Biopharmaceutics Review(s) (Apr. 3, 2014), pp. 1-2: retrieved from: <http://www.accessdata.fda.gov/drugsatfda_docs/nda/2014/125476Orig1s000ClinPharmR.pdf>.
AF Bjorkesten, "Monitoring Treatment Response in Crohn's Disease," Academic Dissertation: University of Helsinki (Feb. 28, 2014), pp. 1-6, 24, 33.
"Annex 1: Summary of Product Characteristics", Jun. 16, 2014, Retrieved from: http://www.ema.europa.eu/docs/en_GB/document_library/EPAR_-_Product_Information/human/002782/WC500168528.pdf, retrieved on Feb. 29, 2016.
Rosario, M. et al., "DOP058 Pharmacokinetic and pharmacodynamic relationship and immunogenicity of vedolizumab in adults with inflammatory bowel disease: Additional results from the Gemini 1 and 2 Studies" Journal of Crohn's and Colitis, vol. 8, Feb. 1, 2014, pp. 42-43.
Parikh, A. et al. "Vedolizumab for the treatment of active ulcerative colitis: a randomized controlled phase 2 dose-ranging study", Inflammatory Bowel Diseases, John Wiley & Sons, Inc. United States, vol. 18, No. 8, Jul. 31, 2012. pp. 1470-1479.
Rosario, M. et al., "P489 Exposure-response relationship during vedolizumab induction therapy in adults with ulcerative colitis" Journal of Crohn's and Colitis, vol. 8, Feb. 1, 2014, p. 488 sec. 270.
Sands, B. et al., "Effects of Vedolizumab Induction Therapy for Patients with Crohn's Disease in Whom Tumor Necrosis Factor Antagonist Treatment Failed", Gastroenterology, vol. 147, No. 3, Sep. 1, 2014, pp. 618-627.
Colombel et al. Therapeutic Drug Monitoring of Biologies for Inflammatory Bowel Disease (Inflamm Bowel Dis 2012; 18:349-358). (Year: 2012).
Fasanmade et al. Population pharmacokinetic analysis of infliximab in patients with ulcerative colitis. Eur J Clin Pharmacol (2009) 65:1211-1228 (Year: 2009).
Fasanmade et al. Serum albumin concentration: a predictive factor of infliximab pharmacokinetics and clinical response in patients with ulcerative colitis. Int J Clin Pharmacol Ther. May 2010;48(5):297-308. (Year: 2010).
Dirks et al. Population Pharmacokinetic Modeling of Vedolizumab in Patients With Ulcerative Colitis or Crohn's Disease. Gastroenterology, 146(5) Suppl 2, S-591, M01225, May 2014. (Year: 2014).
Ordas et al., Anti-TNF Monoclonal Antibodies in Inflammatory Bowel Disease: Pharmacokinetics-Based Dosing Paradigms. Clin Pharmacol Ther. Apr. 2012;91 (4):635-46 (Year: 2012).
Van Hees et al., An index of inflammatory activity in patients with Crohn's disease. Gut, 1980, 21, 279-286 (Year: 1980).
French et al. Exposure-Response Relationship of Vedolizumab Treatment in Adults With Ulcerative Colitis. Gastroenterology, May 2014, vol. 146, Issue 5, Supplement 1, p. S-5 92. Abstract Mo1 229 (Year: 2014).
McKnight W., Faster clearance of vedolizumab associated with less mucosal healing in UC. Internal Medicine News. Dec. 15, 2014. (Year: 2014).
International Preliminary Report on Patentability for Application No. PCT/US2015/000476, dated Jun. 27, 2017.
Extended European Search Report (ESSR) and Search Opinion issued from the European Patent application No. 15873834.4, dated May 16, 2018.
Feagan et al, "Efficacy and Safety of a Humanized alpha.4.beta.7 Antibody in Active Crohn's Disease (CD). Gastroenterology," 124(4)(suppl 1):A25-A26. Abstract 178 (2003).
Feuerstein, J.D., Nguyen, G.C., Kupfer, S.S., Falck-Ytter, Y. & Singh, S. American Gastroenterological Association Institute guideline on therapeutic drug monitoring in inflammatory bowel disease. Gastroenterology 153, 827-34 (2017).
Mitrev, N., et al. Review article: Consensus statements on therapeutic drug monitoring of anti-tumour necrosis factor therapy in inflammatory bowel diseases. Aliment Pharmacol Ther 46, 1037-53 (2017).
NCT00619489; Long Term Safety of Vedolizumab (MLN0002) in Patients With Ulcerative Colitis and Crohn's Disease.
NCT00655135; Phase 2 Study of the Safety and Efficacy of LDP-02 in Mildly to Moderately Active Crohn's Patients.
NCT01177228; Study of Vedolizumab Following Multiple Intravenous Doses in Patients With Ulcerative Colitis.
NCT02163421; Bioavailability and Pharmacokinetics of Vedolizumab in Healthy Participants Following Single Subcutaneous Administration.
NCT02768532; Value of Pharmacokinetic Assays in the Prediction of Induction and Maintenance Therapeutic Response in Crohn's Disease (VEDO-PREDIRESP).
NCT03724929; Value of Pharmacokinetic Assays in the Prediction of Therapeutic Response in Ulcerative Colitis (PREDIRESPUC).
Papamichael, K., et al. Appropriate therapeutic drug monitoring of biologic agents for patients with inflammatory bowel diseases. Clin Gastroenterol Hepatol 17, 1655-68.e3 (2019).
Scholz C, Wyant T, Leach T, Sankoh S, Mould DR, Patella M, et al, Clinical pharmacology of vedolizumab (MLN0002) in patients with active ulcerative colitis. P164 poster (2009).
Scholz et al., "Clinical Pharmacology of Vedolizumab (MLN0002) in Patients with Active Ulcerative Colitis," ECCO Annual Meeting Hamburg, Germany Feb. 5, 2009.
Shivashankar Raina et al: "Effect of Serum Albumin Levels on Efficacy of Vedolizumab in Patients with Crohn's Disease", Gastroenterology, Elsevier Inc, US, Apr. 22, 2017 (Apr. 22, 2017), XP085106026, ISSN: 0016-5085, DOI: 10.1016/50016-5085(17)31593-7.
Vande Casteele, N., Herfarth, H., Katz, J., Falck-Ytter, Y. & Singh, S. American Gastroenterological Association Institute technical review on the role of therapeutic drug monitoring in the management of inflammatory bowel diseases. Gastroenterology 153, 835-57.e6 (2017).
Ward, M.G., Sparrow, M.P. & Roblin, X. Therapeutic drug monitoring of vedolizumab in inflammatory bowel disease: current data and future directions. Therap Adv Gastroenterol 11, 1756284818772786 (2018).
Osterman et al., Aliment Pharmacol Ther 49:408-418 (2019).

* cited by examiner

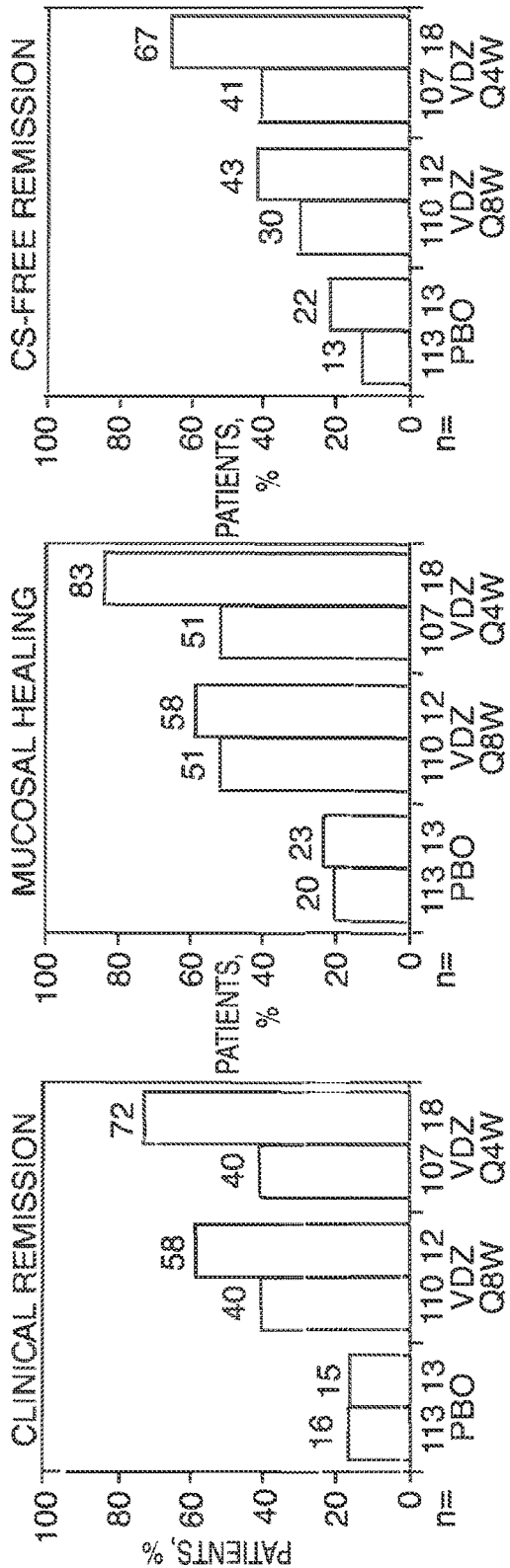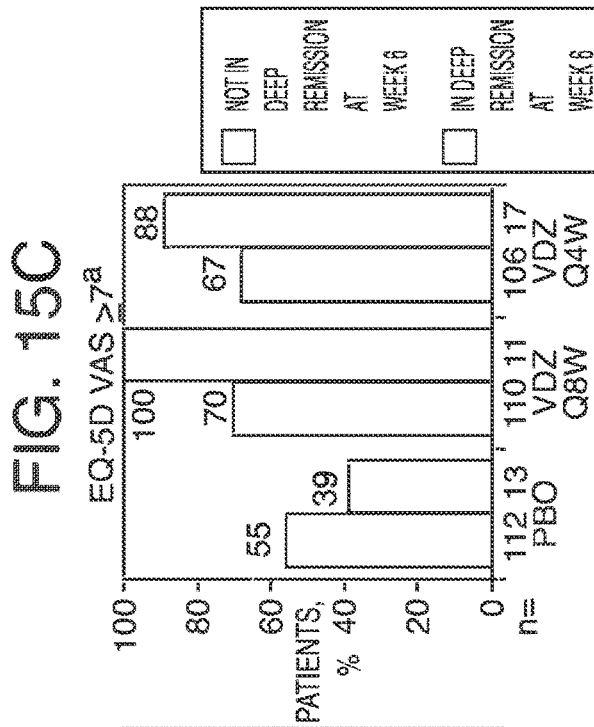

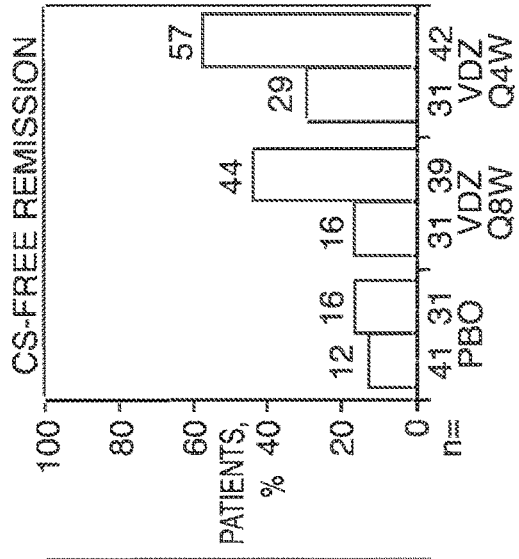
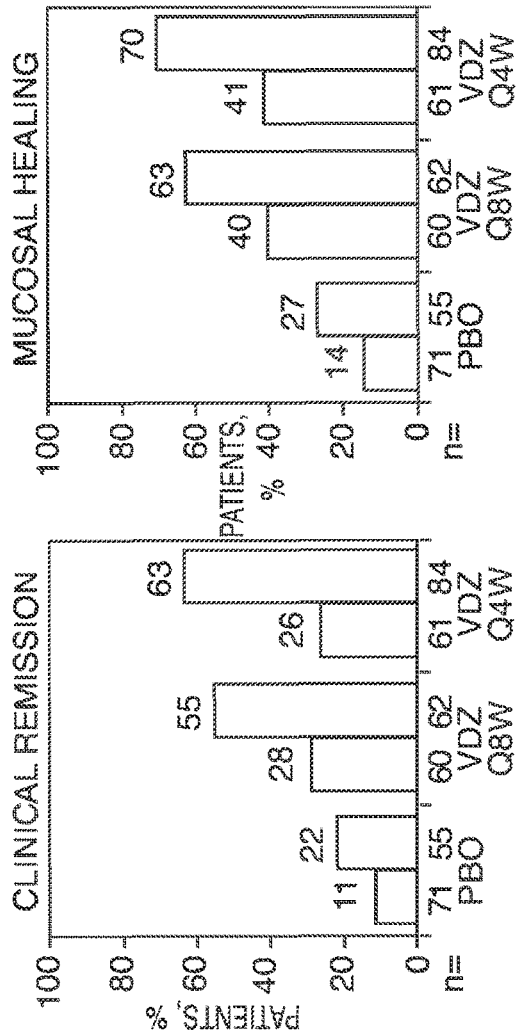
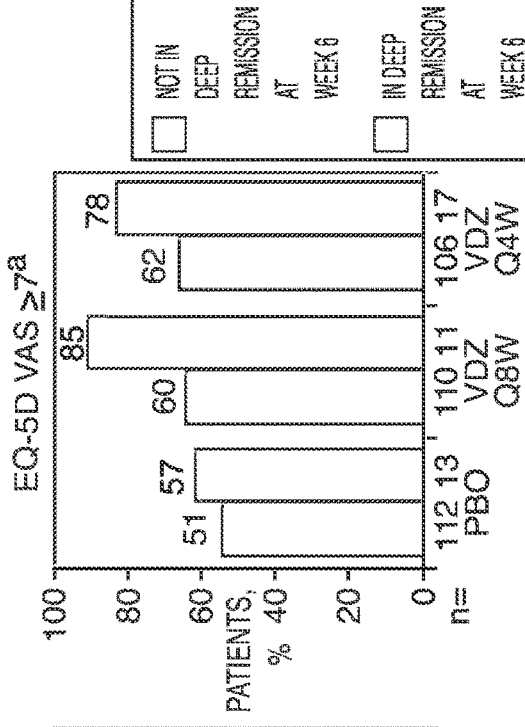
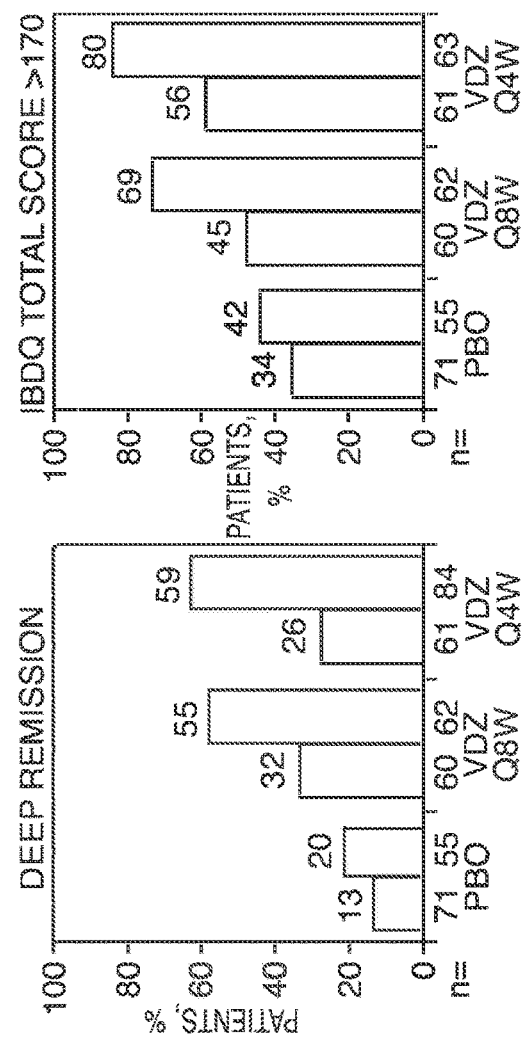

PREDICTING OUTCOME OF TREATMENT WITH AN ANTI-α4β7 INTEGRIN ANTIBODY

RELATED APPLICATIONS

This application is a Continuation Application of U.S. application Ser. No. 15/538,869, filed Jun. 22, 2017, which is a United States National Phase under 35 U.S.C. § 371 of International Application No. PCT/US2015/000476, filed on Dec. 23, 2015, which claims the benefit of U.S. Provisional Application 62/096,636 filed on Dec. 24, 2014, U.S. Provisional Application 62/117,750 filed on Feb. 18, 2015 and U.S. Provisional Application 62/132,917 filed on Mar. 13, 2015. The entire contents of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jun. 21, 2017, is named 079259-0898-SEQLIST-KC.txt and is 13 kb in size.

BACKGROUND

Inflammatory bowel disease (IBD), such as ulcerative colitis and Crohn's disease, for example, can be a debilitating and progressive disease involving inflammation of the gastrointestinal tract. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *New Engl. J. Med.*, 325:928-937 (1991) and Podolsky, *New Engl. J. Med.*, 325:1008-1016 (1991). As the disease progresses, treatment progresses into regimens that expose patients to progressive risk of side effects and loss of quality of life.

Integrin receptors are important for regulating both lymphocyte recirculation and recruitment to sites of inflammation (Carlos, T. M. and Harlan, J. M., *Blood,* 84:2068-2101 (1994)). The human α4β7 integrin has several ligands, one of which is the mucosal vascular addressin MAdCAM-1 (Berlin, C., et al., *Cell* 74: 185-195 (1993); Erle, D. J., et al., *J. Immunol.* 153:517-528 (1994)), which is expressed on high endothelial venules in mesenteric lymph nodes and Peyer's patches (Streeter, P. R., et al., *Nature* 331:41-46 (1998)). As such, the α4β7 integrin acts as a homing receptor that mediates lymphocyte migration to intestinal mucosal lymphoid tissue (Schweighoffer, T., et al., *J. Immunol.* 151: 717-729 (1993)).

Antibodies against human α4β7 integrin, such as murine monoclonal antibody Act-1 (mAb Act-1), interfere with α4β7 integrin binding to mucosal addressin cell adhesion molecule-1 (MAdCAM-1) present on high endothelial venules in mucosal lymph nodes. Act-1 was originally isolated by Lazarovits, A. I., et al., *J. Immunol.* 133:1857-1862 (1984), from mice immunized with human tetanus toxoid-specific T lymphocytes and was reported to be a mouse IgG1/κ antibody. Subsequent analysis of the antibody by Schweighoffer, T., et al., *J. Immunol.* 151:717-729 (1993) demonstrated that it can bind to a subset of human memory CD4+ T lymphocytes which selectively express the α4β7 integrin. Entyvio™ vedolizumab, an anti-α4β7 integrin monoclonal antibody (mAb) with structural features derived from Act-1, is indicated for treating ulcerative colitis (UC) and Crohn's disease (CD). Studies reporting the activity of vedolizumab in treating these disorders (Feagen et al. *NEJM* 369:699-710 (2013) and Sandborn et al. *NEJM* 369:711-721 (2013)) showed varying levels of success depending on the disorder and nature of prior therapies. As these were lengthy studies and there are a growing number of treatment options available to patients, there is a need to identify patients who can benefit from vedolizumab therapy early in their treatment. Expedient and accurate treatment decisions lead to effective management of the disease.

SUMMARY OF THE INVENTION

The invention relates to the identification of patients who can respond to therapy comprising an anti-α4β7 antibody, such as vedolizumab. Early in the course of treatment, e.g., with vedolizumab, factors measured from the patient or from biological samples of the patient indicate whether a patient is likely to respond to treatment.

In one aspect, pharmacokinetics or pharmacodynamics factors can indicate whether a patient will respond to treatment with an anti-α4β7 antibody, such as vedolizumab. As higher therapeutic mAb trough concentrations have been associated with greater efficacy, understanding determinants of mAb clearance may optimize dosing regimens. Applicants have identified the problem, and characterized anti-α4β7 antibody, such as vedolizumab, pharmacokinetic factors in patients with UC and CD, identified clinically relevant determinants of anti-α4β7 antibody, such as antibody clearance, and described the pharmacokinetic-pharmacodynamic relationship using population modeling.

In some embodiments, a pharmacokinetics factor is mean serum trough concentration. In other embodiments, a pharmacokinetics factor is therapeutic antibody clearance. In an embodiment, a pharmacodynamic factor is the amount of antibody bound to α4β7 integrin. In another embodiment, a pharmacodynamic factor is the amount of unbound α4β7 integrin.

In one embodiment, a method for treating a patient having inflammatory bowel disease (IBD) with an anti-α4β7 antibody, such as vedolizumab, comprises administering two doses of the anti-α4β7 antibody to a patient suffering from IBD, wherein the second dose is administered about two weeks after the first dose is administered to the patient; waiting a period of time about four weeks; measuring the patient's serum concentration of the anti-α4β7 antibody; and administering one or more further doses of the anti-α4β7 antibody to the patient if the patient's serum concentration, e.g., a trough serum concentration, of the antibody is at least 8 μg per ml. In some embodiments, the waiting period is two weeks or about two to five weeks. In an embodiment, the method comprises administering two doses of vedolizumab to a patient suffering from IBD, wherein the second dose is administered about two weeks after the first dose is administered to the patient; waiting a period of time about four weeks; measuring the patient's serum concentration of vedolizumab; and administering one or more further doses of vedolizumab to the patient if the patient's serum concentration, e.g., a trough serum concentration, of the antibody is at least 8 μg per ml. In some embodiments, the patient's serum concentration of the anti-α4β7 antibody, e.g., vedolizumab, may be at least 10, 12, 14, 17, 20, 25, 30, 35, or 40 μg per ml. In an embodiment, a patient who is likely to respond to the anti-α4β7 antibody, e.g., vedolizumab has a serum concentration, e.g., a trough serum concentration of greater than 17 μg/ml, greater than 25 μg/ml, or greater than 35 μg/ml. In another embodiment, the patient's serum concentration of anti-α4β7 antibody, e.g., vedolizumab, may be selected from the group consisting of 12-25 µg per ml, 15-17 µg per ml, 17-25 µg per ml, 12-40 µg per ml, and 17-40 µg ml.

In another embodiment, a method for treating a patient having inflammatory bowel disease (IBD) with an anti-α4β7 antibody, such as vedolizumab comprises the steps of administering at least one dose of vedolizumab to the patient suffering from IBD; waiting a period of at least two weeks, measuring the patient's serum concentration of vedolizumab; and administering one or more further doses of vedolizumab to the patient if the patient's serum concentration is at least 8 µg per ml. In some embodiments, the waiting period is about two to five weeks.

In another aspect, clinical measures during early treatment can indicate whether a patient will respond to treatment with an anti-α4β7 antibody, such as vedolizumab.

In one embodiment, the patient can have mucosal healing. In another embodiment, the patient can have deep remission. In an embodiment, the method for treating a patient can comprise measuring an endoscopic subscore, e.g., from the Mayo score, wherein the anti-α4β7 antibody, e.g., vedolizumab is continued with an endoscopic score of less than 3. The endoscopic score can be less than 2.5, less than 2, between 0 and 2, 1, or equal to or less than 1 (≤1) or less than 1 ((<1). In another embodiment, the method for treating a patient can comprise measuring the Crohn's Disease Activity Index (CDAI). In another embodiment, the method for treating a patient can comprise measuring the number, size or severity of fistulae. In an embodiment, the endoscopic score is a simple endoscopic score for Crohn's Disease (SES-CD). In some embodiments, the SES-CD can be in the range of 0 to 6, ≤6, ≤5 or no more than 4 (≤4). In some embodiments, the SES-CD is decreased by 25%, 35%, 40%, 45%, 50%, 55%, 60% or 65% from baseline. In one embodiment, the SES-CD is decreased 50% from baseline. In some embodiments, the method for treating a patient can comprise measuring the amount of ulceration in the digestive tract. In some embodiments, the method for treating a patient can comprise measuring mucosal healing. In some embodiments of mucosal healing, ulceration is decreased or absent.

In another aspect, measures of inflammation can indicate whether a patient will respond to treatment with an anti-α4β7 antibody, such as vedolizumab. Measures of inflammation include amounts of fecal calprotectin, amounts of C-reactive protein (CRP) and amount of albumin. In some embodiments, the method comprises measuring the fecal calprotectin concentration. Treatment with the antibody, e.g., vedolizumab can be continued with a fecal calprotectin concentration of less than 1500 µg/g. The fecal calprotectin concentration can be less than 1250 µg/g, less than 1000 µg/g, less than 750 µg/g, less than 500 µg/g, less than 400 µg/g, less than 300 µg/g, less than 250 µg/g, between 200-1200 µg/g, between 350 to 800 µg/g, between 300-1000 µg/g, <50 µg/g, <100 µg/g, <150 µg/g, <200 µg/g, ≤250-499 µg/g, or between 500 to 900 µg/g.

In some embodiments, treatment with an anti-α4β7 antibody, e.g., vedolizumab can be continued if the fecal calprotectin is reduced to less than 50% of the baseline or concentration before treatment. The fecal calprotectin can be reduced to less than 45%, less than 40%, less than 35%, less than 30%, less than 25%, less than 20%, between 10-55%, between 10-30%, between 15-35%, between 15-45%, or between 20-40% of the baseline or concentration before treatment.

In some embodiments, methods described herein comprise measuring albumin concentration. An albumin concentration greater than 3.2 g/dL further identifies the patient for continued treatment with an anti-α4β7 antibody, e.g., vedolizumab. The albumin concentration can be greater than 3.5 g/dL, greater than 4.0 g/dL, or greater than 4.7 g/dL, in the range of 3.3 to 5.0 g/dL, in the range of 3.5 to 5.0 g/dL, in the range of 3.8 to 5.0 g/dL or in the range of 4.0 to 5.0 g/dL.

In one aspect, the invention relates to therapeutic methods which further include the step of continuing, stopping, discontinuing or halting a therapy accordingly where factors measured as described herein indicate whether there is continued benefit of the therapy.

In one embodiment, a method of identifying a patient for continued treatment with an anti-α4β7 antibody comprises the steps of: measuring the concentration of the anti-α4β7 antibody in a sample of serum obtained from a patient suffering from inflammatory bowel disease (IBD) and who received at least one dose of an anti-α4β7 antibody within the previous two months; and identifying the patient for continued treatment with the anti-α4β7 antibody if the serum concentration in the sample is at least 8 µg per ml. The patient may have received at least one dose of the anti-α4β7 antibody within the previous month. In another embodiment, the patient received at least two doses of the anti-α4β7 antibody within the previous four months; and the method identifies the patient for continued treatment with the anti-α4β7 antibody if its serum concentration in the sample is at least 8 µg per ml four weeks after the second dose, e.g., four weeks after the dose at week 2. The patient may have received at least two doses of the anti-α4β7 antibody within the previous three months or the previous two months. In some embodiments, the patient's serum concentration of the anti-α4β7 antibody may be at least 10, 12, 14, 17, 20, 25, 30, 35, or 40 µg per ml. In another embodiment, the patient's serum concentration of the anti-α4β7 antibody may be selected from the group consisting of 12-25 µg per ml, 15-17 µg per ml, 17-25 µg per ml, 12-40 µg per ml, and 17-40 µg ml.

In one embodiment, a method of identifying a patient for continued treatment with vedolizumab comprises the steps of: measuring the concentration of vedolizumab in a sample of serum obtained from a patient suffering from inflammatory bowel disease (IBD) and who received at least two doses of vedolizumab within the previous four months; and identifying the patient for continued treatment with vedolizumab if the serum concentration in the sample is at least 8 µg per ml four weeks after the second dose, e.g., four weeks after the dose at week 2. The patient may have received at least two doses of vedolizumab within the previous three months or the previous two months. In some embodiments, the patient's serum concentration of vedolizumab may be at least 10, 12, 14, 17, 20, 25, 30, 35, or 40 µg per ml. In another embodiment, the patient's serum concentration of vedolizumab may be selected from the group consisting of 12-25 µg per ml, 15-17 µg per ml, 17-25 µg per ml, 12-40 µg per ml, and 17-40 µg ml.

In another embodiment, the invention relates to a method of identifying a patient for continued treatment with vedolizumab, the method comprising the steps of: measuring the concentration of vedolizumab in a sample of serum obtained from a patient suffering from inflammatory bowel disease (IBD) and who received at least one dose of vedolizumab within the previous two months; and identifying the patient for continued treatment with vedolizumab if the serum concentration in the sample is at least 8 µg per ml. The patient may have received at least one dose of vedolizumab within the previous month. In some embodiments, the patient's serum concentration of vedolizumab may be at least 10, 12, 14, 17, 20, 25, 30, 35, or 40 µg per ml. In another embodiment, the patient's serum concentration of vedolizumab may be selected from the group consisting of 12-25 µg per ml, 15-17 µg per ml, 17-25 µg per ml, 12-40 µg per ml, and 17-40 µg ml.

In another aspect, continuing treatment includes maintaining remission of IBD.

In one embodiment, the invention relates to a method for maintaining remission of inflammatory bowel disease (IBD) in a patient, wherein the patient had received at least one dose of an anti-α4β7 antibody in the previous two months, the method comprising: obtaining a serum sample from the patient; measuring the concentration of the anti-α4β7 antibody in the sample; administering the anti-α4β7 antibody thereafter every eight weeks if the concentration is at least 8 µg per ml. In some embodiments, the patient's serum concentration of the anti-α4β7 antibody may be at least 10, 12, 14, 17, 20, 25, 30, 35, or 40 µg per ml. In another embodiment, the patient's serum concentration of the anti-α4β7 antibody may be selected from the group consisting of 12-25 µg per ml, 15-17 µg per ml, 17-25 µg per ml, 12-40 µg per ml, and 17-40 µg ml.

In one embodiment, the invention relates to a method for maintaining remission of inflammatory bowel disease (IBD) in a patient, wherein the patient had received at least one dose of vedolizumab in the previous two months, the method comprising: obtaining a serum sample from the patient; measuring the concentration of vedolizumab in the sample; administering vedolizumab thereafter every eight weeks if the concentration is at least 8 µg per ml. In some embodiments, the patient's serum concentration of vedolizumab may be at least 10, 12, 14, 17, 20, 25, 30, 35, or 40 µg per ml. In another embodiment, the patient's serum concentration of vedolizumab may be selected from the group consisting of 12-25 µg per ml, 15-17 µg per ml, 17-25 µg per ml, 12-40 µg per ml, and 17-40 µg ml.

In one aspect, evaluation of a patient early in treatment with an anti-α4β7 antibody, such as vedolizumab, indicates that the patient is in deep remission. In an embodiment, the invention relates to a method for treating a patient having inflammatory bowel disease (IBD) with vedolizumab, comprising: providing two doses of vedolizumab, wherein the second dose is about two weeks after the first; waiting about four weeks; and continuing to treat the patient with vedolizumab if the patient is in deep remission, wherein determining deep remission comprises measuring an endoscopic subscore for the patient. The patient can be determined to be in deep remission and continue to receive the anti-α4β7 antibody, e.g., vedolizumab, if the endoscopic subscore is 0 to 1. The method can further comprise determining a patient-reported outcome score, wherein a determination of deep remission comprises 0 to 1 for both the endoscopic subscore and the patient reported outcome score. The patient reported outcome score can comprise a rectal bleeding subscore. The patient reported outcome score can comprise a stool frequency subscore. The method can further comprise measuring the fecal calprotectin concentration. Treatment with an anti-α4β7 antibody, e.g., vedolizumab, can be continued with a fecal calprotectin concentration of less than 1500 µg/g. The fecal calprotectin concentration can be less than 1250 µg/g, less than 1000 µg/g, less than 750 µg/g, less than 500 µg/g, less than 400 µg/g, less than 300 µg/g, less than 250 µg/g, between 200-1200 µg/g, between 350 to 800 µg/g, between 300-1000 µg/g, <50 µg/g, <100 µg/g, <150 µg/g, <200 µg/g, ≤250-499 µg/g, or between 500 to 900 µg/g.

In some embodiments, treatment with the anti-α4β7 antibody, e.g., vedolizumab, can be continued if the fecal calprotectin is reduced to less than 50% of the baseline or concentration before treatment. The fecal calprotectin can be reduced to less than 45%, less than 40%, less than 35%, less than 30%, less than 25%, less than 20%, between 10-55%, between 10-30%, between 15-35%, between 15-45%, or between 20-40% of the baseline or concentration before treatment.

In an embodiment, a vedolizumab-treated patient is in deep remission and can continue to be administered vedolizumab if the vedolizumab trough serum concentration is at least 25 µg/ml, at least 27 µg/ml, at least 30 µg/ml, at least 32 µg/ml or at least 34 µg/ml.

In one aspect, the invention relates to a method for identifying a patient for continued treatment with an anti-α4β7 antibody, the method comprising the steps of: measuring the clearance of the anti-α4β7 antibody in a biological sample obtained from a patient suffering from inflammatory bowel disease (IBD) and who was administered at least two doses of the anti-α4β7 antibody within the previous four months; and identifying the patient for continued treatment with the anti-α4β7 antibody if the clearance in the patient is less than 0.25 L/day. In some embodiments, the patient was administered at least one dose of the anti-α4β7 antibody within the previous two months, the patient was administered at least two doses of the anti-α4β7 antibody within the previous three months or the previous two months, or, the patient was administered at least one dose of the anti-α4β7 antibody within the previous two months or within the previous month. The clearance may be less than 0.20 L/day or between 0.1 and 0.2 L/day.

In one aspect, the invention relates to a method for identifying a patient for continued treatment with vedolizumab, the method comprising the steps of: measuring the clearance of vedolizumab in a biological sample obtained from a patient suffering from inflammatory bowel disease (IBD) and who was administered at least two doses of vedolizumab within the previous four months; and identifying the patient for continued treatment with vedolizumab if the clearance in the patient is less than 0.25 L/day. The clearance may be less than 0.20 L/day or between 0.1 and 0.2 L/day.

In some embodiments, the patient was administered at least two doses of vedolizumab within the previous three months or the previous two months.

In another aspect, the invention relates to a method for identifying a patient for continued treatment with vedolizumab, the method comprising the steps of: measuring the clearance of vedolizumab in a biological sample obtained from a patient suffering from inflammatory bowel disease (IBD) and who was administered at least one dose of vedolizumab within the previous two months; and identifying the patient for continued treatment with vedolizumab if the clearance in the patient is less than 0.25 L/day. The clearance may be less than 0.20 L/day or between 0.1 and 0.2 L/day. In some embodiments, the patient was administered at least one dose of vedolizumab within the previous month. In some embodiments, the patient was administered at least two doses of vedolizumab within the previous month.

The invention further relates to assays for use in measuring the factors described herein for identifying a patient who will respond to treatment with an anti-α4β7 antibody, such as vedolizumab. In some embodiments the assay is a pharmacokinetic assay for circulating anti-α4β7 antibody. In an embodiment, the assay may measure high or sustained positive levels of anti-α4β7 antibody, such as at least 8, 10, 12, 14, 17, 20, 25, 30, 35, or 40 µg per ml in a serum sample from a patient, e.g., for predicting the ability to respond or maintain a response or remission of the IBD afflicting the patient. In an embodiment, the serum concentration of the anti-α4β7 antibody may be measured by a sandwich ELISA assay. In an embodiment, the serum concentration of the anti-α4β7 antibody may be measured in an antibody bridging assay.

In some embodiments, the assay for use in measuring the factors described herein for identifying a patient who will respond to treatment with an anti-α4β7 antibody, such as vedolizumab, is a pharmacodynamic assay for α4β7 integrin, e.g., on circulating lymphocytes. In an embodiment, low or minimum levels of free a4[37 integrin, such as less than 10%, less than 7%, less than 5% or less than 3% free α4β7 integrin, may predict the effectiveness of the anti-α4β7 antibody. In an embodiment, the free α4β7 integrin may be measured by the amount of MAdCAM binding to the α4β7 integrin. In another embodiment, the free α4β7 integrin may be measured by the amount of anti-α4β7 antibody binding to the α4β7 integrin.

In some embodiments, for use in measuring the factors described herein for identifying a patient who will respond to treatment with an anti-α4β7 antibody, such as vedolizumab, the assay measures immune response to the anti-α4β7 antibody. In an embodiment, a low or absent immune response to anti-α4β7 antibody may predict the ability to respond or maintain a response or remission of the IBD afflicting the patient.

The method may further comprise measuring the fecal calprotectin concentration. Treatment with the anti-α4β7 antibody, such as vedolizumab may be continued with a fecal calprotectin concentration of less than 1500 μg/g. The fecal calprotectin concentration may be less than 1250 μg/g, less than 1000 μg/g, less than 750 μg/g, less than 500 μg/g, less than 400 μg/g, less than 300 μg/g, less than 250 μg/g, between 200-1200 μg/g, between 350 to 800 μg/g between 300-1000 μg/g, <50 μg/g, <100 μg/g, <150 μg/g, <200 μg/g, ≤250-499 μg/g, or between 500 to 900 μg/g, in a sample from a patient who is likely to respond to the anti-α4β7 antibody, such as vedolizumab.

In some embodiments, treatment with the anti-α4β7 antibody, such as vedolizumab can be continued if the fecal calprotectin is reduced to less than 50% of the baseline or concentration before treatment. The fecal calprotectin can be reduced to less than 45%, less than 40%, less than 35%, less than 30%, less than 25%, less than 20%, between 10-55%, between 10-30%, between 15-35%, between 15-45%, or between 20-40% of the baseline or concentration before treatment.

In one aspect, a method for treating a human patient having inflammatory bowel disease (IBD), the method comprises: selecting a human patient having IBD and having a serum concentration of vedolizumab which is at least 8 μg per ml at a time point that is four weeks after a second dose of vedolizumab, wherein a first dose of vedolizumab was administered to the subject two weeks prior to the second dose of vedolizumab; and administering vedolizumab to the human patient having IBD, thereby treating the human patient having IBD. In one embodiment, the first dose of vedolizumab comprises 300 mg. In one embodiment, the second dose of vedolizumab comprises 300 mg. In one embodiment, the patient received the first and the second dose intravenously. In some embodiments, the patient had an inadequate response with, lost response to, or was intolerant to a TNF blocker.

One embodiment provided herein is an in vitro method for determining the responsiveness of a human patient having Inflammatory Bowel Disease (IBD) to treatment with vedolizumab, the method comprising measuring the concentration of vedolizumab in a blood sample from the patient by contacting the blood sample with an anti-vedolizumab antibody, wherein the sample is obtained about four weeks following administration of a second dose of vedolizumab, wherein a first dose of vedolizumab was administered to the subject two weeks prior to the second dose of vedolizumab, and wherein a vedolizumab concentration of at least 8 μg per ml in the blood sample indicates that the patient is responsive to treatment with vedolizumab, and a concentration of less than 8 μg per ml in the blood sample indicates that the patient is not responsive to treatment with vedolizumab. In one embodiment, the method further comprises administering vedolizumab to the patient. In one embodiment, the first dose of vedolizumab comprises 300 mg. In one embodiment, the second dose of vedolizumab comprises 300 mg. In one embodiment, the patient received the first and the second dose intravenously. In some embodiments, the patient had an inadequate response with, lost response to, or was intolerant to a TNF blocker.

BRIEF DESCRIPTION OF THE DRAWINGS

FIGS. 15A-15D show clinical, and FIGS. 15E and 15F show HRQoL, outcomes at week 52 in patients in or not in deep remission (definition 1) at week 6.

FIGS. 16A-16D show clinical, and FIGS. 16 E and 16F show HRQoL, outcomes at week 52 in patients in or not in deep remission (definition 2) at week 6.

DETAILED DESCRIPTION

Figure 1:
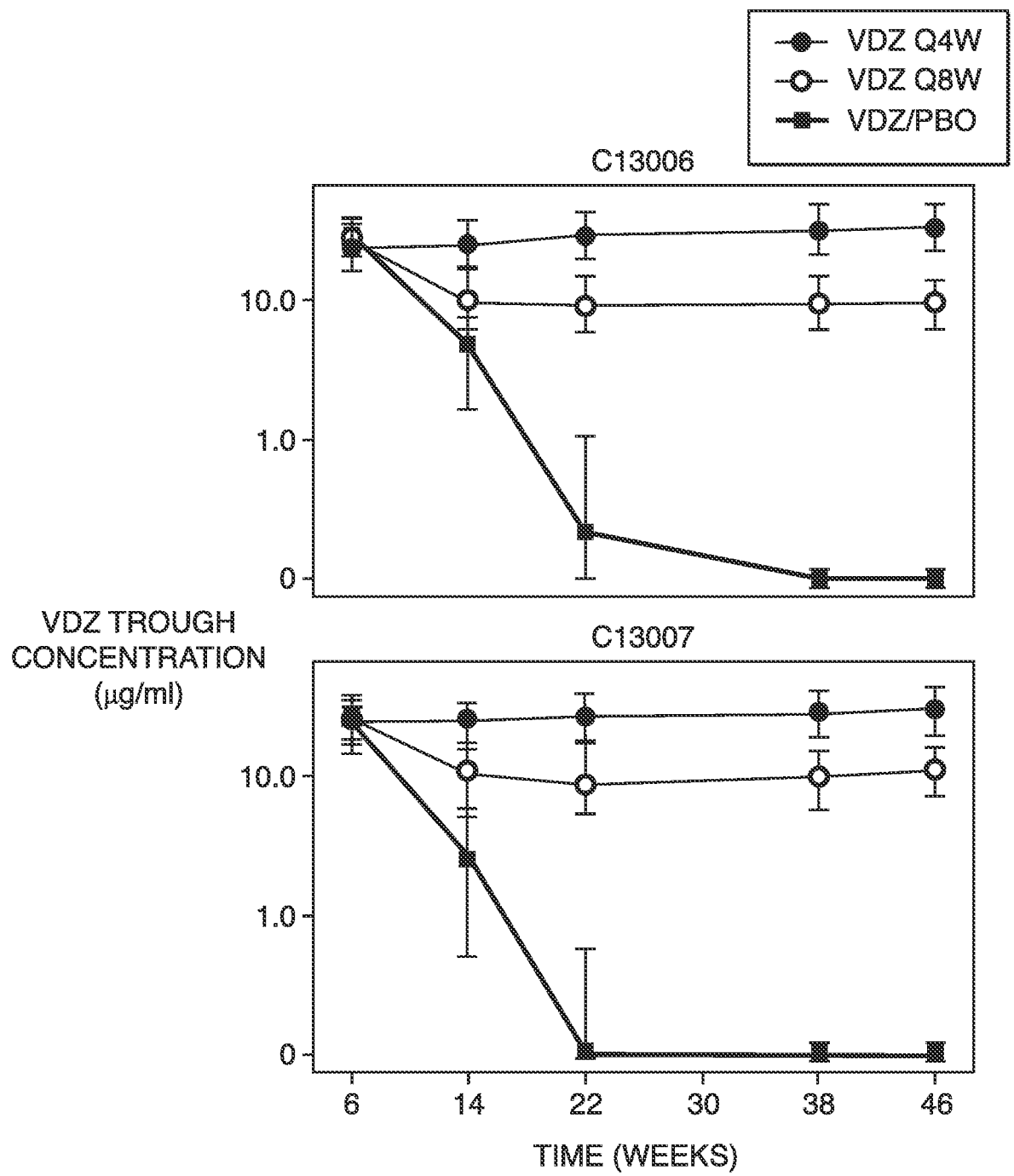
FIG. 1 shows the median (interquartile range) of observed vedolizumab trough serum concentration versus nominal sampling time in patients with UC (GEMINI 1) and patients with CD (GEMINI 2) during maintenance treatment with vedolizumab 300 mg Q4W or Q8W or placebo. All patients (including those in the placebo group) received 2 doses of vedolizumab 300 mg during induction (at weeks 0 and 2).

The invention relates to methods for treating with an anti-α4β7 antibody, e.g., vedolizumab, a patient having inflammatory bowel disease (IBD), methods for identifying a patient for continued treatment with the antibody, such as vedolizumab, and methods for maintaining remission of IBD in a patient.

Not all patients with inflammatory bowel diseases who receive treatment with an anti-α4β7 antibody, such as vedolizumab, respond to the treatment and some do not respond fully to treatment. Due to the morbidity of these diseases, there is a need to quickly identify those patients who respond to anti-α4β7 antibody therapy and those who do not respond. The responders can then continue on the therapy, and the non-responders can be started on alternative therapies. This application relates to the surprising discovery that a patient's serum concentration and/or clearance rate of the anti-α4β7 antibody early during a course of anti-α4[37 antibody treatment can be determined and used to identify or select patients who are responding to treatment and will continue to respond to additional doses of the anti-α4β7 antibody, and non-responders.

Vedolizumab, a humanized monoclonal antibody that binds specifically to the $\alpha_4\beta_7$ integrin, is indicated for the treatment of patients with moderately to severely active ulcerative colitis (UC) and Crohn's disease (CD). Vedolizumab has a novel gut-selective mechanism of action that differs from that of other currently marketed biologic agents for the treatment for inflammatory bowel disease (IBD), including natalizumab and tumor necrosis factor-α (TNF-α) antagonists. By binding to cell surface—expressed $\alpha_4\beta_7$, vedolizumab blocks the interaction of a subset of memory gut-homing T lymphocytes with mucosal addressin cell adhesion molecule-1 (MAdCAM-1) expressed on endothelial cells. Consequently, migration of these cells into inflamed intestinal tissue is inhibited.

The pharmacokinetics of other therapeutic monoclonal antibodies used for the treatment of UC and CD have been previously reported. Several factors are associated with accelerated clearance of these antibodies including the presence of anti-drug antibodies, sex, body size, concomitant immunosuppressant use, disease type, albumin concentration, and degree of systemic inflammation. Furthermore, a consistent relationship between efficacy and exposure, in distinction to drug dose, has been observed for many of these agents, such that higher trough drug concentrations are associated with greater efficacy. Differences in drug clearance may be an important explanation for this observation. Therefore, a better understanding of the determinants of clearance for therapeutic antibodies may result in optimization of drug regimens.

In previous studies, single-dose pharmacokinetics, pharmacodynamics ($\alpha_4\beta_7$ receptor saturation), safety, and tolerability of vedolizumab were investigated over a dose range of 0.2 to 10 mg/kg in healthy volunteers (intravenous [IV] infusion) (unpublished data). After reaching peak concentrations, vedolizumab serum concentrations fell in a generally biexponential fashion until concentrations reached approximately 1 to 10 ng/mL. Thereafter, concentrations appeared to fall in a nonlinear fashion. The multiple-dose pharmacokinetics and pharmacodynamics of vedolizumab have been investigated following IV infusions of 0.5 and 2 mg/kg in patients with CD and infusion of 2, 6, and 10 mg/kg in patients with UC. Vedolizumab pharmacokinetics was generally linear following an IV infusion over the dose range of 2 to 10 mg/kg in patients with UC. After multiple-dose administration, rapid and near complete $\alpha_4\beta_7$ receptor saturation was achieved following the first dose of vedolizumab.

The efficacy and safety of vedolizumab induction and maintenance therapy were demonstrated in patients with UC in the GEMINI 1 trial (ClinicalTrials.gov number, NCT00783718) and in patients with CD in the GEMINI 2 (ClinicalTrials.gov number, NCT00783692) and GEMINI 3 (ClinicalTrials.gov number, NCT01224171) trials. The exposure-response (efficacy) relationships of vedolizumab in patients with UC and CD for induction and maintenance therapy have been presented elsewhere.

Definitions

As used herein, the "trough" serum concentration of an antibody refers to the concentration just before the next dose.

"Clinical remission" or "remission" as used herein with reference to ulcerative colitis subjects, refers to a complete Mayo score of less than or equal to 2 points and no individual subscore greater than 1 point. Crohn's disease "clinical remission" refers to a Crohn's Disease Activity Index (CDAI) score of 150 points or less. The "Harvey-Bradshaw Index" (HBI) is a simpler version of the CDAI for data collection purposes. It consists of only clinical parameters including general well-being, abdominal pain, number of liquid stools per day, abdominal mass, hematocrit, body weight, medications to control diarrhea and presence of complications, and requires only a single day's worth of diary entries. Magnetic resonance enterography (MREn) is being evaluated as a method to measure remission.

"Endoscopic remission" as used herein, refers to a condition with a low endoscopic score. An example of a method to assess the endoscopic score in ulcerative colitis is flexible sigmoidoscopy. The endoscopic score in ulcerative colitis can be the Mayo subscore. An example of a method to assess the endoscopic score in Crohn's disease is ileocolonoscopy. The endoscopic score in Crohn's disease can be the simple endoscopic score for Crohn's Disease (SES-CD). The SES-CD can include measures such as the size of ulcers, the amount of ulcerated surface, the amount of affected surface and whether and to what extent the alimentary canal is narrowed.

A "clinical response" as used herein with reference to ulcerative colitis subjects refers to a reduction in complete Mayo score of 3 or greater points and 30% from baseline, (or a partial Mayo score of 2 or greater points and 25% or greater from baseline, if the complete Mayo score was not performed at the visit) with an accompanying decrease in rectal bleeding subscore of 1 or greater points (≥1) or absolute rectal bleeding score of 1 or less point (≤1). A "clinical response" as used herein with reference to Crohn's disease subjects refers to a 70 point or greater decrease in CDAI score from baseline (week 0). The terms "clinical response" and "response" e.g., alone without any adjective, are used interchangeably herein.

"Endoscopic response" as used herein, refers to a percentage decrease in an endoscopic score from baseline (e.g., at screening or just prior to initial dose). In Crohn's disease, endoscopic response can be assessed by a simple endoscopic score for Crohn's Disease (SES-CD).

"Baseline" as used herein describes a value of a parameter which is measured prior to the initial dose of a treatment. It can refer to a measurement of a sample obtained the same day, the day before, during the week before initial treatment, i.e., at a time period before the first dose when little change is expected until after the first dose and values of the measurement obtained after the first dose can be compared to this baseline value to represent the change caused by the dose.

"Mucosal healing" as used herein as used herein with reference to ulcerative colitis subjects, refers to a Mayo endoscopic subscore of less than or equal to 1. In reference to Crohn's disease, "fistula healing" results in closure or elimination of fistulae. In another reference to Crohn's disease, mucosal healing refers to an improvement in the amount or severity of wounding in mucosae, e.g., the digestive tract. For example, mucosal healing can refer to a decrease in the amount, size or severity of one or more than one ulcer in the digestive tract. In another example, mucosal healing refers to a decrease in one or more parameters selected from the group consisting of wall thickness, enhanced bowel wall contrast, mural edema, ulceration and perienteric vascularity. Such mucosal healing can be expressed as an SES-CD score, or a Magnetic Resonance Index of Activity (MaRIA) score. Complete mucosal healing in Crohn's disease includes absence of ulceration.

The "MaRIA score" is the sum of the scores, e.g., as measured by magnetic resonance enterography, of various mucosal healing parameters for each segment of colon and the terminal ileum (e.g., ileum, ascending colon, transverse colon, descending colon, sigmoid, and rectum).

"Corticosteroid (CS)-free remission" as used herein, refers to patients using oral corticosteroids at baseline who have discontinued corticosteroid use and are in clinical remission at week 52.

"European Quality of Life-5 Dimension (EQ-5D) visual analogue scale (VAS)" as used herein, refers to a questionnaire which is a validated (ahrq.gov/rice/eq5dproj.htm, "U.S. Valuation of the EuroQol EQ-5D™ Health States", accessed 8 Aug. 2012, Bastida et al. BMC Gastroenterology 10:26-(2010), Konig et al. European Journal of Gastroenterology & Hepatology 14:1205-1215 (2002)) instrument used to measure general health-related quality of life (HRQOL) in patients and includes five domains—mobility, self-care, usual activities, pain/discomfort, and anxiety/depression. Patients choose the level of health problems they currently have on each item as "None", "Moderate", or "Extreme" and are scored a 1, 2, or 3, respectively. A composite EQ-5D score can be calculated from the individual scores to assess overall HRQOL. The EQ-5D Visual Analog Scale (VAS) score is a self-assigned rating of overall health using a 20 cm visual, vertical scale, with a score of 0 as the worst and 100 as best possible health. The EQ-5D and EQ-5D VAS have been shown in many studies to be valid and reliable instruments for measuring HRQOL in patients with GI diseases. A decrease of ≥0.3 points in the EQ-5D score represents a clinically meaningful improvement in HRQOL for patients. An increase of greater than or equal to 7 points in the EQ-5D VAS score represents a clinically meaningful improvement in HRQOL for patients.

The "Inflammatory Bowel Disease Questionnaire" ((IBDQ) questionnaire" (Irvine Journal of Pediatric Gastroenterology & Nutrition 28:S23-27 (1999)) is used to assess quality of life in adult patients with inflammatory bowel disease, ulcerative colitis, or Crohn's Disease and includes 32 questions on four areas of HRQOL: Bowel Systems (10 questions), Emotional Function (12 questions), Social Function (5 questions), and Systemic Function (5 questions). Patients are asked to recall symptoms and quality of life from the last 2 weeks and rate each item on a 7-point Likert scale (higher scores equate to higher quality of life). A total IBDQ score is calculated by summing the scores from each domain; the total IBDQ score ranges from 32 to 224. An IBDQ total score greater than 170 is characteristic of the health related quality of life (HRQoL) of patients in remission.

As used herein, "induction therapy" is an initial stage of therapy, wherein a patient is administered a relatively intensive dosing regimen of a therapeutic agent. The therapeutic agent, e.g., antibody, is administered in a way that quickly provides an effective amount of the agent suitable for certain purposes, such as inducing immune tolerance to the agent or for inducing a clinical response and ameliorating disease symptoms (see WO 2012/151247 and WO 2012/151248, incorporated herein by reference).

As used herein, "maintenance therapy" is after induction therapy and is administered in a way that continues the response achieved by induction therapy with a stable level of therapeutic agent, e.g., antibody. A maintenance regimen can prevent return of symptoms or relapse of disease, e.g., IBD (see WO 2012/151247 and WO 2012/151248, incorporated herein by reference). A maintenance regimen can provide convenience to the patient, e.g., be a simple dosing regimen or require infrequent trips for treatment.

The cell surface molecule, "α4β7 integrin," or "α4β7," is a heterodimer of an $\alpha_4$ chain (CD49D, ITGA4) and a $\beta_7$ chain (ITGB7). Each chain can form a heterodimer with an alternative integrin chain, to form $\alpha_4\beta_1$ or $\alpha_E\beta_7$. Human $\alpha_4$ and $\beta_7$ genes (GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 include vascular cell adhesion molecule (VCAM), fibronectin and mucosal addressin (MAdCAM (e.g., MAdCAM-1)). The α4β7 integrin mediates lymphocyte trafficking to GI mucosa and gut-associated lymphoid tissue (GALT) through adhesive interaction with mucosal addressin cell adhesion molecule-1 (MAdCAM-1), which is expressed on the endothelium of mesenteric lymph nodes and GI mucosa.

The term "antibody" herein is used in the broadest sense and specifically covers full length monoclonal antibodies, immunoglobulins, polyclonal antibodies, multispecific antibodies (e.g. bispecific antibodies) formed from at least two full length antibodies, e.g., each to a different antigen or epitope, and individual antigen binding fragments, including dAbs, scFv, Fab, F(ab)'$_2$, Fab', including human, humanized and antibodies from non-human species and recombinant antigen binding forms such as monobodies and diabodies.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

"Antigen binding fragments" of an antibody comprise at least the variable regions of the heavy and/or light chains of an anti-α4β7 antibody. For example, an antigen binding fragment of vedolizumab comprises amino acid residues 20-131 of the humanized light chain sequence of SEQ ID NO:2. Examples of such antigen binding fragments include Fab fragments, Fab' fragments, scFv and F(ab')$_2$ fragments of a humanized antibody known in the art. Antigen binding fragments of the humanized antibody of the invention can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CH$_I$ domain and hinge region of the heavy chain. In one aspect, antigen binding fragments inhibit binding of α4β7 integrin to one or more of its ligands (e.g. the mucosal addressin MAdCAM (e.g., MAdCAM-1), fibronectin).

The terms "Fc receptor" or "FcR" are used to describe a receptor that binds to the Fc region of an antibody. In one aspect, the FcR is a native sequence human FcR. In another aspect, the FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review in M. Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. aim Med.* 126:33-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and for regulating the persistence of immunoglobulin G (IgG) and albumin in the serum (reviewed by Rath et al., *J. Clin. Immunol.* 33 Suppl 1:S9-17 (2013)).

The term "hypervariable region" when used herein refers to the amino acid residues of an antibody which are responsible for antigen binding and are found in the "variable domain" of each chain. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disease as well as those in which the disease or its recurrence is to be prevented. Hence, the patient to be treated herein may have been diagnosed as having the disease or may be predisposed or susceptible to the disease. The terms "patient" and "subject" are used interchangeably herein.

Treatment of IBD with Anti-α4β7 Antibodies

In one aspect, the invention relates to a method of treating IBD in a subject comprising administering to the subject an anti-α4β7 antibody described herein in an amount effective to treat IBD, e.g., in humans. The human patient or subject may be an adult (e.g., 18 years or older), an adolescent, or a child. A pharmaceutical composition comprising an anti-α4β7 antibody can be used as described herein for treating IBD in a subject suffering therefrom.

The anti-α4β7 antibody can bind to an epitope on the α4 chain (e.g., humanized MAb 21.6 (Bendig et al., U.S. Pat. No. 5,840,299), on the β7 chain (e.g., FIB504 or a humanized derivative (e.g., Fong et al., U.S. Pat. No. 7,528,236)), or to a combinatorial epitope formed by the association of the α4 chain with the β7 chain. In one aspect, the antibody binds a combinatorial epitope on the α4β7 complex, but does not bind an epitope on the α4 chain or the β7 chain unless the chains are in association with each other. The association of a4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Such antibodies can bind α4β7 but not bind α4β1, and/or not bind $\alpha_E\beta7$, for example. In another aspect, the anti-α4β7 antibody binds to the same or substantially the same epitope as the Act-1 antibody (Lazarovits, A. I. et al., *J. Immunol.*, 133(4): 1857-1862 (1984), Schweighoffer et al., *J. Immunol.*, 151(2): 717-729, 1993; Bednarczyk et al., *J. Biol. Chem.*, 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf of Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

In one aspect, the anti-α4β7 antibodies for use in the treatments are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:4, CDR2, SEQ ID NO:5 and CDR3, SEQ ID NO:6) of the mouse Act-1 antibody and suitable human heavy chain framework regions; and also contain a light chain that contains the 3 light chain CDRs (CDR1, SEQ ID NO:7, CDR2, SEQ ID NO:8 and CDR3, SEQ ID NO:9) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In one aspect, the anti-α4β7 antibody is vedolizumab. Vedolizumab (also called MLN0002, ENTYVIO™ or KYNTELES™) is a humanized immunoglobulin (Ig) G1 mAb directed against the human lymphocyte integrin α4β7. Vedolizumab binds the α4β7 integrin, antagonizes its adherence to MAdCAM-1 and as such, impairs the migration of gut homing leukocytes into GI mucosa. Vedolizumab is an integrin receptor antagonist indicated for adult patients with moderately to severely active UC or CD who have had an inadequate response with, lost response to, or were intolerant to a tumor necrosis factor (TNF) blocker or immunomodulator, or had an inadequate response with, were intolerant to, or demonstrated dependence on corticosteroids. For UC, vedolizumab is for inducing and maintaining clinical response, inducing and maintaining clinical remission, improving endoscopic appearance of the mucosa, and/or achieving corticosteroid-free remission. For CD, vedolizumab is for achieving clinical response, achieving clinical remission, and/or achieving corticosteroid-free remission. In some embodiments, corticosteroid-free remission is achieved through a tapering regimen during continued treatment with vedolizumab.

In another aspect, the humanized anti-α4β7 antibody for use in the treatment comprises a heavy chain variable region comprising amino acids 20 to 140 of SEQ ID NO:1, and a light chain variable region comprising amino acids 20 to 131 of SEQ ID NO:2 or amino acids 21 to 132 of SEQ ID NO:3. If desired, a suitable human constant region(s) can be present. For example, the humanized anti-α4β7 antibody can comprise a heavy chain that comprises amino acids 20 to 470 of SEQ ID NO:1 and a light chain comprising amino acids 21 to 239 of SEQ ID NO:3. In another example, the humanized anti-α4β7 antibody can comprise a heavy chain that comprises amino acids 20 to 470 of SEQ ID NO:1 and a light chain comprising amino acids 20 to 238 of SEQ ID NO:2. The humanized light chain of vedolizumab (e.g., Chemical Abstract Service (CAS, American Chemical Society) Registry number 943609-66-3), with two mouse residues switched for human residues, is more human than the light chain of LDP-02, another humanized anti-α4β7 antibody. In addition, LDP-02 has the somewhat hydrophobic, flexible alanine 114 and a hydrophilic site (Aspartate 115) that is replaced in vedolizumab with the slightly hydrophilic hydroxyl-containing threonine 114 and hydrophobic, potentially inward facing valine 115 residue.

Further substitutions to the humanized anti-α4β7 antibody sequence can be, for example, mutations to the heavy and light chain framework regions, such as a mutation of isoleucine to valine on residue 2 of SEQ ID NO:10; a mutation of methionine to valine on residue 4 of SEQ ID NO:10; a mutation of alanine to glycine on residue 24 of SEQ ID NO:11; a mutation of arginine to lysine at residue 38 of SEQ ID NO:11; a mutation of alanine to arginine at residue 40 of SEQ ID NO:11; a mutation of methionine to isoleucine on residue 48 of SEQ ID NO:11; a mutation of isoleucine to leucine on residue 69 of SEQ ID NO:11; a mutation of arginine to valine on residue 71 of SEQ ID NO:11; a mutation of threonine to isoleucine on residue 73 of SEQ ID NO:11; or any combination thereof; and replacement of the heavy chain CDRs with the CDRs (CDR1, SEQ ID NO:4, CDR2, SEQ ID NO:5 and CDR3, SEQ ID NO:6) of the mouse Act-1 antibody; and replacement of the light chain CDRs with the light chain CDRs (CDR1, SEQ ID NO:7, CDR2, SEQ ID NO:8 and CDR3, SEQ ID NO:9) of the mouse Act-1 antibody.

The present invention provides, in a first aspect, a method for treating a patient having inflammatory bowel disease (IBD) with an anti-α4β7 antibody, e.g., vedolizumab. In this aspect, the method comprises determining pharmacokinetic factors of the patient. In some embodiments, the method comprises selecting for treatment a patient who has low clearance of the antibody. The method comprises measuring the concentration of the anti-α4β7 antibody in a biological sample from the patient, e.g., blood, serum, plasma, stool, bowel fluid, saliva, inflammatory exudate, at a time, e.g., at least one, two, three, four, five or six weeks, after receiving at least one prior dose of the antibody. The measurement provides an indication of clearance, for which "low" is defined by the various methods, and results criteria thereof described herein, of obtaining a clearance indication. An indication of clearance may result from the measurement of the concentration of anti-α4β7 antibody in the sample, which may be used alone or used in a calculation, as described herein, of the rate the anti-α4β7 antibody is eliminated from the body, e.g., the blood volume. The calculation may be based on knowledge of the amount of anti-α4β7 antibody in the prior dose, the size of the patient or blood volume, the number of days between the day of the prior dose of the anti-α4β7 antibody and the day of obtaining the sample for measurement or from a pharmacokinetics model, e.g., a model as described herein. In some embodiments, measurement of serum concentration of anti-α4β7 antibody may be an indicator of clearance. Clearance may be affected or further illustrated by other parameters, such as pharmacodynamic factors, clinical factors, inflammation or immune response factors, whose measurement may be used in combination with the measurement of anti-α4β7 antibody. An indication of clearance, alone or in combination with measurements of one or more other parameters, may be used to predict response to anti-α4β7 antibody treatment, identify a patient who is responding to anti-α4β7 antibody treatment, select a patient for further treatment with anti-α4β7 antibody or monitor the effectiveness of the anti-α4β7 antibody during treatment. Low clearance or sufficient amounts of anti-α4β7 antibody in the patient, e.g., at the time of sampling, indicates that further dosing with anti-α4β7 antibody will provide benefit in the treatment of IBD. In some embodiments, a method wherein low clearance is indicated, measured or calculated at end of induction comprises further treatment of the patient for maintenance of response or remission, achieving corticosteroid-free remission, improving endoscopic appearance of the mucosa. Preferably, a patient who has low clearance of the antibody may be characterized, a) by a rate of antibody, e.g., vedolizumab, clearance that is less than about 0.25 L/day, less than 0.20 L/day, between 0.1 to 0.2 L/day, less than 0.15 L/day or less than 0.1. L/day; and/or b) by a serum concentration of antibody, e.g., vedolizumab, that is at least 8 μg per ml, 10 μg per ml, 12 μg per ml, 14 μg per ml, 17 μg per ml, 20 μg per ml, 25 μg per ml, 30 μg per ml, 35 μg per ml, or 40 μg per ml or has a range of 12-25 μg per ml, 15-17 μg per ml, 17-25 μg per ml, 12-40 μg per ml, and 17-40 μg ml.

In one embodiment, the method for treating a patient having inflammatory bowel disease (IBD) with an anti-α4β7 antibody, e.g., vedolizumab comprises the steps of selecting a human patient having IBD from a group of two or more patients having or suffering from IBD that has, at a time point of four weeks after receiving a second dose of vedolizumab, where the first dose of vedolizumab was administered to the subject two weeks prior to the second dose, a serum concentration of at least about 8, about 10, about 12, about 14, about 17, about 20, about 25, about 30, about 35, or about 40 μg per ml. Specifically, the patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml. In some embodiments, the patient received the prior dose of vedolizumab about two weeks, about three weeks, about four weeks, about five weeks or about six weeks prior to the sampling for serum vedolizumab measurement. Once such a patient is selected from a group of patients, he or she is administered vedolizumab to treat the IBD.

In another aspect, the present invention provides a method for treating a patient having inflammatory bowel disease (IBD) with an anti-α4β7 antibody, e.g., vedolizumab. In some embodiments, the method using vedolizumab comprises the steps of administering two doses of vedolizumab to a patient suffering from IBD, wherein the second dose is administered about two weeks after the first dose is administered to the patient; waiting a period of time of at least two weeks, at least three weeks, about four weeks or five weeks; measuring the patient's serum concentration of vedolizumab; and administering one or more further doses of vedolizumab to the patient if the patient's serum concentration is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml.

Alternatively, at least one dose of the anti-α4β7 antibody, e.g., vedolizumab may be administered to a patient suffering from IBD, waiting at least about two weeks, or optionally, a period of two to five weeks, and then measuring the patient's serum concentration of vedolizumab and administering one or more further doses of vedolizumab to the patient if the patient's serum concentration is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml.

In another aspect, the present invention provides a method of identifying a patient (e.g., a patient having mucosal healing) for continued treatment with vedolizumab. The method may comprise the steps of measuring the concentration of vedolizumab in a sample of serum obtained from a patient suffering from IBD and who received at least two doses of vedolizumab within the previous four months (e.g., within the previous three months, within the previous two months), and identifying the patient for continued treatment with vedolizumab if the serum concentration in the sample is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml. In some embodiments, the patient received the last prior dose, e.g., the second dose, of vedolizumab about four weeks prior to the sampling for serum vedolizumab measurement. In other embodiments, the patient received the last prior dose 3 to 8 weeks prior to the sampling for serum vedolizumab measurement.

Alternatively, the method of identifying a patient for continued treatment with an anti-α4β7 antibody, e.g., vedolizumab may comprise the steps of measuring the concentration of vedolizumab in a sample of serum obtained from a patient suffering from IBD and who received at least one dose of vedolizumab within the previous one or two months, and identifying the patient for continued treatment with vedolizumab if the serum concentration in the sample is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml. In some embodiments, the patient received the prior dose of vedolizumab about two weeks, about three weeks, about four weeks, about five weeks or about six weeks prior to the sampling for serum vedolizumab measurement.

Alternatively, at least one dose of the anti-α4β7 antibody, e.g., vedolizumab may be administered to a patient suffering from IBD, waiting at least about two weeks, or optionally, a period of two to five weeks, and then measuring the patient's serum concentration of vedolizumab and administering one or more further doses of vedolizumab to the patient if the patient's serum concentration is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml.

Vedolizumab may be administered by any suitable method, such as by one or more of intravenous injection, subcutaneous injection, or infusion. In some embodiments, vedolizumab is administered at a dose of 50 mg, 100 mg, 180 mg, 300 mg, or 600 mg. In some embodiments, the vedolizumab is administered, for example subcutaneously, at a dose of 0.5 mg/kg, 1.0 mg/kg, 1.5 mg/kg, 2.0 mg/kg, 2.5 mg/kg, 3.0 mg/kg. 4.0 mg/kg, or 5.0 mg/kg, at a dose of 108 mg, 216 mg, 160 mg or 165 mg. The vedolizumab may be administered once per day, per week, per month, or per year. A vedolizumab dosing regimen may have an initial or induction phase and a maintenance phase. An induction phase may be one or more than one, e.g., two, three or four doses, of high amounts or without long times, such as only one week, two weeks, three weeks or four weeks between each dose. For example, an induction regimen may have two doses, one at day (week) zero and one at week 2 (day 14). A maintenance phase, e.g., to maintain remission of the IBD, may have lower doses or doses further apart than in the induction phase. In some embodiments, the vedolizumab is administered at zero, two and six weeks (induction), and then every four weeks or every eight weeks thereafter (maintenance). Patients with IBD refractory to other therapies may need longer induction periods, e.g., 8, 10 or 12 weeks, before beginning maintenance therapy. In an embodiment, vedolizumab is administered intravenously at zero, two and six weeks, then every eight weeks thereafter. In some embodiments, vedolizumab is administered one or more times, and then at least one month, at least six months, or at least one year later, vedolizumab is again administered one or more times. In some embodiments, 300 mg vedolizumab may be administered by intravenous infusion at zero, two, and six weeks, and then at four weeks intervals or eight week intervals thereafter. In some embodiments, 300 mg vedolizumab may be administered by intravenous infusion at zero, two, and six weeks, and then at two-, three- or four-week intervals, 108 mg of vedolizumab may be administered subcutaneously. Treatment methods using anti-α4β7 integrin antibodies are described in publication nos. U.S. 2005/0095238, WO2012151248 and WO 2012/151247.

In some embodiments, the method of identifying a patient for continued treatment with an anti-α4β7 antibody, e.g., vedolizumab may comprise a clinical measure. A clinical measure may be mucosal healing. An endoscopic score decreased from baseline, e.g. 25% less, 35% less, 40% less, 45% less, 50% less, 55% less, 60% less, 65% less, or 75% less than baseline, may indicate mucosal healing. In ulcerative colitis, an endoscopic score of less than 4, less than 3, ≤1, or between 0 and 2 may help identify a patient for continued treatment. In Crohn's disease, a patient with mucosal healing, and thus a candidate for continued treatment with an anti-α4β7 antibody, e.g., vedolizumab, may have an assessment selected from the group consisting of endoscopic response, endoscopic remission, improvement in the MaRIA score, decrease in ulceration, and improvement in a mucosal healing parameter, e.g., an MREn parameter. In one embodiment, a MaRIA score is the sum of each segment calculation, wherein a sum that one would calculate for each segment=(1.56×wall thickness (mm))+(0.02×Relative Contrast Enhancement (RCE), e.g., after administration of intravenous contrast with gadolinium)+(5×edema)+(10×ulceration)). In some embodiments endoscopic response is achieved by about a 25% decrease, about a 40% decrease, about a 50% decrease, about a 60% decrease or about a 75% decrease in SES-CD score from baseline. In some embodiments, endoscopic remission is achieved by an SES-CD score of ≤6, ≤5, ≤4 or ≤3. In some embodiments, mucosal healing is achieved by a MaRIA score of <14, <13, <12, <11, <10, <9, <8, <7, <6, <5 or <4. In some embodiments a decrease in ulceration is selected from the group consisting of a decrease in the size of ulcers, a decrease in the percent of ulcerated surface, a decrease in the percent of affected surface and decrease in the narrowings of the canal. In some embodiments, the size of ulcers is less than 2 cm in diameter, 0.5 to 2 cm in diameter, 0.1 to 0.5 cm in diameter or <0.2 cm diameter. In some embodiments, the ulcerated surface is less than 30%, 10-30%, less than 10%, or 0. In some embodiments the affected surface is less than 75%, 50%-75%, less than 50%, less than 25% or unaffected. In some embodiments, the wall thickness is decreased by about 10%, about 15%, about 20%, about 25%, about 30%, about 20%-40% or more than 45% from baseline. In some embodiments, the bowel wall contrast (RCE) is decreased about 15%, about 20%, about 25%, about 30%, about 35%, about 40%, about 20%-40% or more than 40% from baseline. In some embodiments, the mural edema is decreased by about 25%, about 40%, about 50%, about 60%, about 70%, more than 75%, or about 70%-90% from baseline. In some embodiments, the perienteric vascularity is decreased by about 25%, about 30%, about 40%, about 50%, about 60%, about 50%-70%, about 75% or more than 75% from baseline.

In an embodiment, a Crohn's disease patient who is responsive to vedolizumab has an SES-CD of ≤4 at week 6, 10, 12, 14, 22 or 26 after initiating treatment. In an embodiment, a Crohn's disease patient who is responsive to vedolizumab has an endoscopic response or ≥50% reduction of SES-CD at week 6, 10, 12, 14, 22 or 26 after initiating treatment. In an embodiment, a Crohn's disease patient who is responsive to vedolizumab has a clinical remission or ≥70 or ≥100 point reduction of CDAI score at week 6, 10, 12, or 14 after initiating treatment. In an embodiment, a Crohn's disease patient who is responsive to vedolizumab has a MaRIA score of <15, <12, <10 or <7 at week 6, 10, 12, 14, respectively, globally or on a per segment basis, after initiating treatment. In an embodiment, a Crohn's disease patient who is responsive to vedolizumab has no ulceration at week 14, 22 or 26 after initiating treatment. In an embodiment, a Crohn's disease patient who is responsive to vedolizumab has no fistulae at week 14, 22, 26 or 30 after initiating treatment. A patient who is responsive to vedolizumab may continue to be treated, e.g., may continue a maintenance regimen, with vedolizumab. In one embodiment, a maintenance regimen comprises a dose of vedolizumab once every 2 weeks. In one embodiment, a maintenance regimen comprises a dose of vedolizumab once every 4 weeks. In one embodiment, a maintenance regimen comprises a dose of vedolizumab once every 6 weeks. In one embodiment, a maintenance regimen comprises a dose of vedolizumab once every 8 weeks.

In another aspect, the present invention relates to a method for maintaining remission of inflammatory bowel disease in a patient. The patient may have received at least one dose of vedolizumab in the previous two months, the previous three months or the previous four months. The method may comprise the steps of obtaining a serum sample from the patient, measuring the concentration of vedolizumab in the sample, and administering vedolizumab thereafter every eight weeks if the concentration is at least about 8, about 10, about 12, about 14, about 17, about 20, about 25, about 30, about 35, or about 40 μg per ml. The patient's serum concentration may be between about 12-25, about 15-17, about 17-25, about 12-40, or about 17-40 μg per ml. The patient's serum concentration, e.g., a trough serum concentration, may be greater than 17 μg/ml, greater than 25 μg/ml, or greater than 35 μg/ml. In some embodiments, the patient received the prior dose of vedolizumab about two weeks, about three weeks, about four weeks, about five weeks or about six weeks prior to the sampling for serum vedolizumab measurement.

In yet another aspect of the present invention, a method for continuing to treat an IBD patient with vedolizumab comprises the steps of providing two doses of vedolizumab, wherein the second dose is about two weeks after the first; waiting about four weeks; and continuing to treat the patient with vedolizumab if the patient is in deep remission. Deep remission may be determined by measuring an endoscopic subscore for the patient and is defined as having an endoscopic subscore of 0 to 1. The method may further comprise the step of determining a patient-reported outcome score (e.g., a subscore of 0 to 1). The patient-reported outcome may comprise a rectal bleeding subscore (e.g., 0) and/or a stool frequency subscore (e.g., decrease or no change; 0 or 1).

The invention also relates to a method for identifying a patient for continued treatment with vedolizumab comprising the steps of measuring the clearance of vedolizumab in a biological sample obtained from a patient suffering from IBD and who was administered at least two doses of vedolizumab within the previous four months (e.g., within the previous three months, within the previous two months), and identifying the patient for continued treatment with vedolizumab if the clearance in the patient is less than 0.25 L/day, less than 0.20 L/day, or between 0.1 to 0.2 L/day. The biological sample may be any biological sample, for example, serum, plasma, saliva, urine, or feces. Optionally, the method may further comprise measuring anti-α4β7 antibody antibodies. A low or absent immune response to the anti-α4β7 antibody, e.g., anti-vedolizumab antibody, e.g., a titer of ≥50, ≥125 or ≥575 may further identify the patient for continued treatment with vedolizumab.

Methods to determine whether a patient will respond to treatment with an anti-α4β7 antibody or whether to continue treating a patient with an anti-α4β7 antibody may further comprise measuring albumin concentration. In therapeutic antibody therapy, this can be a reflection of clearance activity, such as ability to bind the neonate FcR. In cases of low serum albumin levels, the anti-α4β7 antibody can have a high clearance. Consequently, a patient with high serum albumin levels may not respond or may take longer to respond to treatment with anti-α4β7 antibody. An albumin concentration greater than about 3.0 g/dL, about 3.2 g/dL, about 4.0 g/dL, about 4.7 g/dL, or about 5.0 g/dL, or in the range of 3.3 to 5.0 g/dL, in the range of 3.5 to 5.0 g/dL, in the range of 3.8 to 5.0 g/dL or in the range of 4.0 to 5.0 g/dL may further identify the patient for continued treatment with the anti-α4β7 antibody, e.g., vedolizumab. The albumin concentration measurement may be accompanied by measurement of patient weight. A high weight patient, e.g., greater than 90 kg, greater than 100 kg, greater than 110 kg, or greater than 120 kg, with low albumin levels, e.g., less than 4.2 g/dL, less than 4.0 g/dL, less than 3.5 g/dL or less than 3.2 g/dL, may have high anti-α4β7 antibody clearance and thus may not respond to therapy with the anti-α4β7 antibody or may need a higher or more frequent dose of the anti-α4β7 antibody for continued treatment.

Clearance, e.g., linear clearance, e.g., the volume of blood which is cleared of drug per unit time, may be calculated/estimated/derived by any appropriate means known to those skilled in the art. For example, clearance may be estimated by population approach or Bayesian methods, e.g., the full Bayesian Markov Chain Monte Carlo (MCMC) method. One method of developing the pharmacokinetic model of linear clearance is described in the Examples. The anti-α4β7 antibody exposure metric, such as trough serum concentration, e.g., serum concentration of anti-α4β7 antibody prior, e.g., 1 day, 2 days, 3 days, 4 days or up to a week prior, to administering a new dose, peak serum concentration, average serum concentration measured at more than one sampling or area under the concentration time curve, is inputted into the model to determine clearance.

Alternatively, the method for identifying a patient for continued treatment with vedolizumab comprising the steps of measuring the clearance of vedolizumab in a biological sample obtained from a patient suffering from IBD can be performed on a patient who was administered at least one dose of vedolizumab within the previous one or two months, and identifying the patient for continued treatment with vedolizumab if the clearance in the patient is less than 0.25 L/day, less than 0.20 L/day, between 0.1 to 0.2 L/day, less than 0.15 L/day or less than 0.1. L/day. The biological sample may be any biological sample, for example, serum, plasma, saliva, urine, or feces.

The method may further comprise measuring an endoscopic subscore. Anti- α4β7 antibody, e.g., vedolizumab treatment may be continued with an endoscopic subscore of less than about 3, less than about 2.5, less than about 2, between about 0-2, or less than or equal to 1.

Fecal levels of calprotectin, a neutrophil cytosolic protein, correlate with endoscopic activity in ulcerative colitis. Typically, a non-diseased subject will have a fecal calprotectin level of less than 50 µg/g. A fecal calprotectin level greater than 50 but less than 150 µg/g may be a sign of possible mucosal inflammation, whereas fecal calprotectin levels greater than 150 µg/g is usually a sign of active inflammation. The methods described herein may further comprise measuring the fecal calprotectin concentration. Higher levels of fecal calprotectin are associated with a greater risk of relapse. Vedolizumab treatment may be continued with a fecal calprotectin concentration of less than 1500 µg/g, less 1250 µg/g, less than 1000 µg/g, less than 750 µg/g, less than 500 µg/g, less than 400 µg/g, less than 300 µg/g, less than 250 µg/g, between 200-1200 µg/g, between 350 to 800 µg/g, between 300-1000 µg/g, <50 µg/g, <100 µg/g, <150 µg/g, <200 µg/g, ≤250-499 µg/g, or between 500 to 900 µg/g. Alternatively, fecal calprotectin may be reduced to less than about 50%, 45%, 40%, 35%, 30%, 25%, 20%, between 10-55%, between 10-30%, between 15-35%, between 15-45% or between 20-40% of the baseline or concentration before treatment. Fecal calprotectin in a stool sample can be measured using the PHICAL test kit (Calpro, Lysaker Norway).

Pharmacokinetic and Pharmacodynamic Assays

The anti-α4β7 antibody, e.g., vedolizumab, serum concentration may be measured by any appropriate means known by those skilled in the art. In one aspect, the vedolizumab serum concentration is measured by a sandwich enzyme-linked immunosorbent assay (ELISA) assay. In another aspect, use of a pharmacodynamic assay, inhibition of MAdCAM-1-Fc binding to α4β7-expressing peripheral blood cells by the anti-α4β7 antibody, e.g., vedolizumab in the blood is used as a measure of the extent of α4β7 saturation by the anti-α4β7 antibody, e.g., vedolizumab.

In an embodiment, the anti-α4β7 antibody amount in serum can be measured in a pharmacokinetic assay. An immobilized phase, such as a microliter plate, vessel or bead is coated with a reagent which specifically binds to the anti-α4β7 antibody. The immobilized reagent is contacted with a patient sample, e.g., serum, which may or may not comprise the anti-α4β7 antibody. After incubation and washing, the anti-α4β7 antibody complexed to the coating reagent is contacted with a reagent which binds to the captured antibody and may be detected, e.g., using a label such as horseradish peroxidase (HRP). The binding reagent may be an anti-human antibody, e.g., polyclonal or monoclonal, which binds to the Fc portion of the anti-α4β7 antibody. Addition of an HRP substrate, such as 3,3',5,5'-tetramethylbenzidine (TMB), can allow signal accumulation, such as color development, that can be measured, e.g., spectrophotographically.

In some embodiments, the coating reagent is an anti-idiotypic antibody which specifically binds to the anti-α4β7 antibody, e.g., its variable region or a portion thereof comprising one or more CDRs, such as heavy chain CDR3, SEQ ID NO:6. The anti-idiotypic anti-α4β7 antibody for use in the assay can be specific for, and thus bind, the α4β7 integrin-binding portion of the anti-α4β7 antibody but is not specific for the Fc portion of the anti-α4β7 antibody and thus does not bind the Fc portion of the anti-α4β7 antibody. The anti-idiotypic anti-α4β7 antibody for use in the assay can be specific for, and thus bind, a variable region of the heavy and/or light chain of anti-α4β7 antibody, e.g., selected from the group consisting of amino acids 20 to 140 of SEQ ID NO:1, amino acids 20 to 131 of SEQ ID NO:2 and amino acids 21 to 132 of SEQ ID NO:3. The anti-idiotypic anti-α4β7 antibody for use in the assay can be specific for, and thus bind, an antigen-binding fragment of the anti-α4β7 antibody. The anti-idiotypic antibody can be isolated from an immunization process using the anti-α4β7 antibody or an α4β7 integrin-binding portion thereof, such as an antibody fragment comprising one or more CDRs, and used as isolated or produced by a recombinant method. In some embodiments, the anti-idiotypic anti-α4β7 antibody is raised against an immunogen comprising heavy chain CDR3, SEQ ID NO:6. In other embodiments, the anti-idiotypic anti-α4β7 antibody is raised against an immunogen comprising a variable region of the heavy and/or light chain of anti-α4β7 antibody, e.g., selected from the group consisting of amino acids 20 to 140 of SEQ ID NO:1, amino acids 20 to 131 of SEQ ID NO:2 and amino acids 21 to 132 of SEQ ID NO:3. In some embodiments, the anti-idiotypic antibody is a monoclonal antibody. In some embodiments, an scFv fragment of the anti-idiotypic antibody is used in the assay. In other embodiments, the intact anti-idiotypic antibody is used in the assay.

Generation of an anti-idiotypic anti-α4β7 antibody can proceed in the following general methods. Immunization of a suitable animal (e.g., mouse, rat, rabbit or sheep) with protein, e.g., anti-α4β7 antibody or an α4β7 integrin binding portion thereof, or fusion protein comprising the portion, can be performed with the immunogen prepared for injection in a manner to induce a response, e.g., with adjuvant, e.g., complete Freund's adjuvant. Other suitable adjuvants include TITERMAX GOLD® adjuvant (CYTRX Corporation, Los Angeles, Calif.) and alum. Small peptide immunogens, such as a fragment comprising a CDR, such as CDR3 of the heavy chain can be linked to a larger molecule, such as keyhole limpet hemocyanin. Mice can be injected in a number of manners, e.g., subcutaneous, intravenous or intramuscular at a number of sites, e.g., in the peritoneum (i.p.), base of the tail, or foot pad, or a combination of sites, e.g., i.p. and base of tail. Booster injections can include the same or a different immunogen and can additionally include adjuvant, e.g., incomplete Freund's adjuvant. Generally, where a monoclonal antibody is desired, a hybridoma is produced by fusing a suitable cell from an immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of animals immunized with the antigen of interest. Cells that produce antibodies can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., *Hybridoma*, 17:299-304 (1998); Zanella et al., *J Immunol Methods*, 156:205-215 (1992); Gustafsson et al., *Hum Antibodies Hybridomas*, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA (e.g., with immunogen immobilized on the microtiter well).

The anti-α4β7 antibody or the anti-idiotypic anti-α4β7 antibody may be produced by expression of nucleic acid sequences encoding each chain in living cells, e.g., cells in culture. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an anti-α4β7 antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety. In an insect system, *Autographa californica* nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In other embodiments, the coating reagent is a ligand of the antibody, such as MAdCAM or an α4β7 integrin-binding fragment thereof or fusion protein comprising an α4β7-integrin binding fragment of MAdCAM fused with a non-MAdCAM protein, such as an immunoglobulin G constant domain. Examples of MAdCAM reagents and fusion proteins are described in PCT publication WO9624673 and U.S. Pat. No. 7,803,904, the entire teachings of which are incorporated herein by reference.

HAHA Assay

The human anti- anti-α4β7 antibody activity (HAHA) can be determined by detecting and/or measuring anti-drug antibodies (ADAs) or antibodies specific to the anti-α4β7 antibody (anti-vedolizumab antibodies). There are a number of options, for example, using a screening and titration assay, a confirmation assay, and a neutralizing assay. Serum samples can be measured first in the screening sample at dilutions, for example, 1:5 and 1:50. Positive samples can be confirmed for specificity, titered, and examined for the ability to neutralize anti-α4β7 antibody, e.g., vedolizumab activity.

A screening assay can use a bridging ELISA in which the plate is coated with the anti-α4β7 antibody. The immobilized anti-α4β7 antibody captures the ADA in the test sample which is bound by an anti-α4β7 antibody conjugated to biotin, which is tagged by horseradish peroxidase (HRP)-labeled streptavidin, then detected with an enzymatic substrate, such as TMB. A positive color development, e.g., as measured in a microplate reader, such as Spectramax, with analytical software, such as SOFTMAX Pro3.1.2, indicates the presence of ADAs in the sample. The assay cut point, e.g., in biotin-avidin-HRP based bridging assay, can be determined by using normal human serum samples as negative controls. The mean absorbance values of the 10 negative control serums can be added to 1.65 times the standard deviation of the negative controls to determine the cut point. Thus, the cut point can allow for approximately a 5% false positive rate. In the presence of 1 μg/mL vedolizumab, low titer responses are interfered with such that they may become undetectable, although high levels of immunogenicity are detectable at vedolizumab concentrations greater than 1 μg/mL. For example, while the standard assay sensitivity can be 0.44 ng/ml, in the presence of 0.5 μg/ml vedolizumab, the sensitivity of the assay can be 180 ng/ml. For these reasons, serum samples can be taken greater than 4 weeks, greater than 8 weeks, greater than 12 weeks or greater than 16 weeks after the final dose of anti-α4β7 antibody. With a longer time period between the prior dose and the sampling, serum drug levels typically can be below the interference level.

Another assay method uses streptavidin coated plates, biotin-labeled anti-α4β7 antibody anchored to streptavidin coated vessels, beads or microtiter plates for the immobilized side of the bridge and heavy metal, such as ruthenium, osmium or rhenium-labeled (e.g., via a sulfo tag) anti-α4β7 antibody for the other side of the bridge. The bridged complex can be built on the plate by stepwise additions and washes between or in solution, with both sides of the bridge contacting diluted serum sample, then transferred to the plate. An example of an assay using this method has a sensitivity of 3.90 ng/ml anti- anti-α4β7 antibody. Detection of the heavy metal labeled bridge complex, e.g., a ruthenium-labeled complex, by electrochemiluminescence (ECL), e.g., in a Meso Scale Discovery Sector Imager 6000 (Rockville, Md.), may be more sensitive than an HRP method and/or have higher tolerance to the amount of anti-α4β7 antibody in the serum. Thus there would not be a need to wait for a delayed sample after the serum drug level lowers. In some embodiments, pretreatment of the serum sample with acid, e.g., acetic acid or low pH glycine, to release the anti-α4β7 antibody from the patient-derived anti- anti-α4β7 antibodies prior to contacting with the bridging anti-α4β7 antibodies can reduce the interference from the drug in the serum. For example, while the standard assay sensitivity can be 3.90 ng/ml, in the presence of 5 μg/ml vedolizumab in serum, the sensitivity of the assay can be 10 ng/ml.

In an embodiment, an assay to detect anti-vedolizumab antibodies in a sample of serum from a patient comprises diluting serum by a standard dilution factor, such as 1:5, 1:25, 1:50, and/or 1:125; treating with acetic acid; combining the acid treated diluted sample with an assay composition comprising a high pH reagent, such as high concentration TRIS buffer for neutralizing the acid, a biotin-labeled vedolizumab and a ruthenium-labeled vedolizumab for a time sufficient to form a bridge with serum-derived anti-vedolizumab antibodies between the two tagged versions of vedolizumab; transferring the complexes to a streptavidin-coated plate; washing the plate so only ruthenium complexed by the antibody bridge is present. Detection of the bound ruthenium-labeled complex and measuring the sample by electrochemiluminescence in the microplate reader can be achieved by adding a read solution such as tripropylamine and applying voltage to stimulate the ruthenium label complexed to the plate via the antibody bridge.

After the initial screening assay, samples can be further tested in a confirmatory assay that uses excess unlabeled anti-α4β7 antibody to demonstrate specificity. Confirmed positive samples can be further assessed for the ability of the HAHA to neutralize the binding of the anti-α4β7 antibody, e.g., vedolizumab to cells. A competitive flow cytometry-based assay was designed to determine the ability of the immune serum to inhibit the binding of labeled vedolizumab to an α4β7 integrin-expressing cell line, RPMI8866, and detection by flow cytometry.

The results can indicate categories of immunogenicity status: Negative: no positive HAHA sample; Positive: at least 1 positive HAHA sample; Transiently positive: at least 1 positive HAHA sample and no consecutive positive HAHA samples; and Persistently positive: at least 2 or more consecutive positive HAHA samples. Negative patients are likely to respond to anti-α4β7 antibody and can continue being treated with the antibody. Persistently positive patients are likely to have high clearance of anti-α4β7 antibody and may not respond to anti-α4β7 antibody treatment. Positive patients may have high clearance of anti-α4β7 antibody and may not respond to anti-α4β7 antibody. Positive patients can have an additional serum sample 2, 3, 4, 5 or 6 weeks after another dose of anti-α4β7 antibody to determine if they are persistently positive or transiently positive. Transiently positive patients are likely to respond to anti-α4β7 antibody treatment and treatment of these patients can be continued.

Titers of immunogenicity levels also may be determined. Titer categories include ≥5 (low), ≥50, ≥125, ≥625 and ≥3125 (high). A patient with a high titer in a positive sample may have high clearance of anti-α4β7 antibody and may not respond to anti-α4β7 antibody treatment. A patient with a low titer in a positive sample may respond to anti-α4β7 antibody treatment.

The invention will be more fully understood by reference to the following examples. They should not, however, be construed as limiting the scope of the invention. All literature and patent citations are incorporated herein by reference.

EXEMPLIFICATION

Example 1

Pharmacokinetic and Pharmacodynamic Modeling

Here, we report a comprehensive population pharmacokinetic and pharmacodynamic analysis of vedolizumab therapy in patients with UC and CD. Our objectives were to (1) characterize the pharmacokinetics of vedolizumab in patients who received repeated IV infusions of vedolizumab 300 mg for up to 52 weeks; (2) identify clinically relevant determinants of vedolizumab clearance in patients; and (3) describe the pharmacokinetic-pharmacodynamic relationship of vedolizumab in patients using MAdCAM-1 as the pharmacodynamic endpoint.

Materials and Methods

Study Design and Sample Collection

Analyses were conducted using vedolizumab serum concentrations obtained from 5 randomized, placebo-controlled clinical studies: a phase 1 study in healthy volunteers, a phase 2 study in patients with active UC (NCT01177228), a phase 3 study in patients with moderately to severely active UC (GEMINI 1 [NCT00783718]), and 2 phase 3 studies in patients with moderately to severely active CD (GEMINI 2 [NCT00783692] and GEMINI 3 [NCT01224171]) (Table S1). The study designs and clinical data for the phase 2 and 3 studies have been previously reported. All study protocols and consent forms were approved by institutional review boards or ethics committees at the study sites, and studies were conducted in accordance with the principles of good clinical practice and the Declaration of Helinski. All patients provided written informed consent before study participation.

Details of the blood sampling times for pharmacokinetic, pharmacodynamic (MAdCAM-1), and anti-drug antibody (ADA) analyses are provided in Table S1. Extensive pharmacokinetic and pharmacodynamic sampling was used in the phase 1 and 2 studies, whereas sparse sampling was used in the phase 3 studies. Pharmacodynamic samples were not collected in GEMINI 3.

TABLE S1

Clinical studies included in vedolizumab population pharmacokinetic/pharmacodynamic analyses

| Study Identifier | Study Design/Study Population | Dosing Regimen | Partipicants Enrolled/With PK | Blood Sampling Times for PK, PD, and ADA Analyses |
|---|---|---|---|---|
| C13009 | Phase 1, single-dose study evaluating PK, PD, safety, and tolerability of VDZ | Single dose VDZ 300 mg IV (n = 13) | Total = 87 VDZ = 62 Placebo = 25 PK = 55 | PK: Day 1 (predose; 35 min and 1, 2, and 12 h postdose). PK and PD: Day 2 (24 |

TABLE S1-continued

Clinical studies included in vedolizumab population pharmacokinetic/pharmacodynamic analyses

| Study Identifier | Study Design/Study Population | Dosing Regimen | Partipicants Enrolled/With PK | Blood Sampling Times for PK, PD, and ADA Analyses |
|---|---|---|---|---|
| | Part 1, open-label; Part 2, double-blind. Healthy subjects (aged 18-45 years). | VDZ 600 mg IV (n = 23) VDZ 600 mg IV (n = 26) Placebo IV (n = 25) | | h postdose), Day 8 (168 h postdose), Day 29 (696 h postdose), Day 57 (1344 h postdose), Day 85 (2016 h postdose), Day 113 (2688 postdose), Day 141 (3360 postdose), Day 169 (4032 postdose), Day 197 (4704 h postdose). |
| C13002 (NCT01177228) | Phase 2, randomized, double-blind, placebo-controlled, PK/PD, multiple-dose, multicenter study. Patients with mildly to moderately active UC (aged 18-70 years). | 4 doses (days 1, 15, 29, and 85) VDZ 2.0 mg/kg IV (n = 13) VDZ 6.0 mg/kg IV (n = 14) VDZ 10.0 mg/kg IV (n = 11) Placebo IV (n = 9) | Total = 47 VDZ = 38* Placebo = 9 PK = 35 | PK and PD:# Day 1 (predose; 2 and 12 h postdose), Day 2 (24 h postdose), Day 3 (48 h postdose), Day 4 (72 h postdose), Day 8 (at anytime), Days 15 and 29 (predose; 2 h postdose), Days 43, 57, 71 (at any time), Day 85 (predose; 2 and 12 h postdose), Day 86 (24 h postdose), Day 87 (48 h postdose), Day 89 (96 h postdose), and at any time on Days 92, 99, 113, 127, 141,155, 169, 183, 197, 211, 225, 239, and 253. ADA: Day 1, 15, 29, and 85 (predose) and Days 57, 113, 141, 169, 197, 225, and 253 |
| GEMINI 1 (NCT00783718) | Phase 3, 52-week, randomized, placebo-controlled, double-blind, multicenter study of efficacy and safety of VDZ induction and maintenance therapy. Patients with moderately to severely active UC and inadequate response to, loss of response to, or intolerance of 1 of more of the following agents: corticosteroids (ex-US only), immunomodulators, or TNF-α antagonists (aged 18-80 years). | Multiple dose Induction (Weeks 0 and 2): VDZ 300 mg IV Placebo Maintenance (for 44 weeks): VDZ 300 mg IV Q4W VDZ 300 mg IV Q8W Placebo | ITT: VDZ = 225 Placebo = 149 Non-ITT: VDZ = 521 ITT: VDZ Q4W = 125 VDZ Q8W = 122 Placebo = 126 Non-ITT: VDZ Q4W = 373 Placebo = 149 PK = 654 | PK: Weeks 0, 2, 6, 22, and 46 (predose [within 30 min before start of infusion] and postdose [within 2 h after start of infusion]); Weeks 14 and 38 (predose); Weeks 4 and 52 (anytime during visit). PD: Weeks 0 and 6 (predose); Week 52. ADA: Weeks 0, 6, 14, 26, 38, 52 (or Early Termination visit), 66 (or Final Safety visit) and at the time of disease exacerbation. Samples were collected predose, if applicable. |
| GEMINI 2 (NCT00783692) | Phase 3, 52-week, randomized, placebo-controlled, double-blind, multicenter study of efficacy and safety of VDZ induction and maintenance therapy. Patients with moderately to severely active CD and demonstrated inadequate response to, loss of response to, or intolerance of 1 of more of the following agents: corticosteroids (ex-US only), immunomodulators, or | Multiple dose Induction (Weeks 0-2): VDZ 300 mg IV Placebo Maintenance (for 44 weeks): VDZ 300 mg IV Q4W VDZ 300 mg IV Q8W Placebo | ITT: VDZ = 220 Placebo = 148 Non-ITT: VDZ = 747 ITT: VDZ Q4W = 154 VDZ Q8W = 154 Placebo = 153 Non-ITT: VDZ Q4W = 506 Placebo = 148 PK = 827 | PK: Weeks 0, 2, 6, 22, and 46 (predose [within 30 min before start of infusion] and postdose [within 2 h after start of infusion]); Weeks 14 and 38 (predose); Weeks 4 and 52 (anytime during visits). PD: Weeks 0 and 6 (predose); Week 52. ADA: Weeks 0, 6, 14, 26, 38, 52 (or Early Termination visit), 66 (or Final Safety visit) and at the time of disease exacerbation. |

TABLE S1-continued

Clinical studies included in vedolizumab population pharmacokinetic/pharmacodynamic analyses

| Study Identifier | Study Design/Study Population | Dosing Regimen | Partipicants Enrolled/With PK | Blood Sampling Times for PK, PD, and ADA Analyses |
|---|---|---|---|---|
| GEMINI 3 (NCT01224171) | Phase 3, 10-week, randomized, placebo-controlled, double-blind, multicenter study of efficacy and safety of VDZ induction therapy. Patients with moderately to severely active CD and demonstrated inadequate response to, loss of response to, or intolerance of 1 of more of the following agents: corticosteroids (ex-US only), immunomodulators, or TNF-α antagonists (aged 18-80 years). | Multiple dose Induction (Weeks 0, 2 and 6) VDZ 300 mg IV | ITT: VDZ = 209 Placebo = 207 TNF-α antagonist failure: VDZ = 158 Placebo = 157 PK = 352 | Samples were collected predose, if applicable. PK: Week 0 (postdose); Week 6 (predose and postdose [within 2 h after start of infusion]); Week 10 (anytime during visit) or Early Termination. ADA: Weeks 0, 6, 10 (or Early Terminatio visit), and 22 (or Final Safety visit). Samples were collected predose, if applicable. |

Assays

Vedolizumab serum concentrations were determined using a sandwich enzyme-linked immunosorbent assay (ELISA), with a lower limit of detection of 0.00125 µg/mL at a 1:100 dilution. The accuracy of the assay was 10.1% coefficient of variation (CV), intra-sample precision ranged from 1.8% to 3.0% CV, and inter-sample precision ranged from 4.0% to 16.0% CV.

To quantitate $\alpha_4\beta_7$ integrin saturation by vedolizumab in peripheral serum, a MAdCAM-1-Fc binding interference flow cytometry assay was developed. In this pharmacodynamic assay, inhibition of MAdCAM-1-Fc binding to $\alpha_4\beta_7$-expressing peripheral blood cells by vedolizumab in the blood is used as a measure of the extent of $\alpha_4\beta_7$ saturation by vedolizumab [1]. The assay, which was developed by Millennium Pharmaceuticals, Inc. (d/b/a Takeda Pharmaceuticals International, Co.), demonstrated an overall intra-sample variability of 6% CV and an intra-subject variability of 20% CV.

The presence of anti-drug antibodies (ADAs) or antibodies specific to the anti-α4β7 antibody (anti-vedolizumab antibodies) was determined using a validated, biotinylated, bridging ELISA and 2 dilutions of serum (1:5 and 1:50). The plate is coated with the anti-α4β7 antibody. The immobilized anti-α4β7 antibody captures the ADA in the test sample. After washing, the bound complex captures an anti-α4β7 antibody conjugated to biotin, which after another wash, captures HRP-labeled streptavidin. When incubated with TMB substrate, a positive color development indicates the presence of ADAs in the sample. All samples that screened positive were further diluted to determine the final ADA titer using standard techniques. If both screening dilutions were negative, the sample was considered negative. Patients were classified as positive for ADAs if antibodies were detected at any visit; otherwise they were classified as negative.

Data Assembly

The dosing, covariate, and pharmacokinetic-pharmacodynamic data were merged and formatted for the population analysis using R, Version 2.10.1 or higher (www.r-project.org). Vedolizumab serum concentration measurements that were missing, or any values with unknown or missing associated observation times, dose times, dose amounts, or dosing intervals, were excluded from the analysis. MAdCAM-1 measurements were treated similarly. All vedolizumab samples reported as below the limit of quantification (BLQ) (n=3189) were not evaluated during the population pharmacokinetic model development. More than half of the BLQ observations (n=1722) were samples obtained prior to the first vedolizumab dose.

Covariates present in the population pharmacokinetic dataset were serum C-reactive protein (CRP), serum albumin, fecal calprotectin, body weight, disease activity (Crohn's Disease Activity Index [CDAI], complete Mayo score, partial Mayo score), Mayo endoscopic subscore, age, sex, ADA status (positive or negative), prior TNF-α antagonist therapy status (naïve or failed), body mass index (BMI), serum globulin, diagnosis (CD or UC), lymphocyte count, and concomitant therapy use (methotrexate, azathioprine, mercaptopurine, or aminosalicylates). The start date and end date of concomitant therapy was populated in the dataset to evaluate the time-dependent effects of concomitant treatments. Covariates with missing data were imputed using different imputation methods, based on the remaining available data (e.g. median of the remaining values). No covariates present in the population pharmacokinetic dataset were missing more than 10% of values.

Population Pharmacokinetic Model Development

The population pharmacokinetic analysis for repeated measures was conducted using a nonlinear mixed effects modeling approach (NONMEM 7, Version 7.2; ICON Development Solutions, Ellicott City, Md., USA) [13]. The base population pharmacokinetic model was developed using the first-order conditional estimation with the η-ε interaction (FOCEI) method and extensively sampled phase 1 and 2 data. Results from the base model were subsequently used as prior information to selectively inform a subset of population pharmacokinetic model parameters in the full covariate model, which was fit to sparse phase 3 data from GEMINI 1, 2, and 3. The full covariate model was fit to the phase 3 data using the full Bayesian Markov Chain Monte Carlo (MCMC) method. All parameter estimates were reported with Bayesian 95% credible intervals (CDIs) as a measure of estimation uncertainty.

Population parameters, including fixed effects parameters (covariate coefficients and structural model parameters) and random effects parameters, were estimated. Interindividual random effect distributions were modeled using exponential variance models for linear clearance ($CL_L$), central compartment volume of distribution ($V_c$), and maximum elimination rate ($V_{max}$), with a full block covariance matrix, whereas residual random effects were described with a proportional model.

A covariate modeling approach emphasizing parameter estimation rather than stepwise hypothesis testing was implemented for the population pharmacokinetic analysis [14]. First, predefined covariate parameter relationships were identified based on exploratory graphics, scientific interest, and mechanistic plausibility. Then a full covariate model was constructed with care to avoid correlation or collinearity in predictors; covariates with correlation coefficients greater than ~0.35 were not simultaneously included as potential predictors. Construction of the full model was also guided by evaluating the adequacy of the study design and covariate data to support quantification of the covariate effects of interest.

Inferences about the clinical relevance of parameters were based on the resulting parameter estimates and measures of estimation precision (Bayesian 95% CDIs) from the full model. In the absence of an exposure-response relationship for efficacy-related clinical endpoints to provide a context for interpretation of pharmacokinetic variability, covariate effect sizes greater than ±25% of the typical population value were proposed as clinically meaningful changes.

Modeling assumptions included log transformation of pharmacokinetic/pharmacodynamic (where appropriate) parameters. In those cases where no physiologic relationship was known a priori, the effects of continuous covariates were modeled using an additive model in the log domain, while the effects of categorical covariates were similarly described:

$$TPV = \exp\left(\theta_n + \sum_l \log\left(\frac{cov_{ml}}{ref_m}\right) \cdot \theta_{(m+n)} + \sum_l^p \theta_{(p+m+n)}^{cov\,pi}\right)$$

where the typical value of a model parameter (TPV) is described as a function of m individual continuous covariates ($cov_{mi}$) and p individual categorical covariates categories; $\theta_n$ is an estimated parameter describing the typical log-transformed pharmacokinetic parameter value for an individual with covariates equal to the reference covariate values ($cov_{mi}=ref_m$); and $\theta_{(m+n)}$ and $\theta_{(p+m+n)}$ are estimated parameters describing the magnitude of the covariate-parameter relationship.

The final population pharmacokinetic model and parameter estimates were investigated with a predictive check method. This method is similar to the posterior predictive check, but assumes that parameter uncertainty is negligible relative to interindividual and residual variance. Five hundred Monte Carlo simulation replicates of the original dataset were compared with the distribution of the same exposure metric in the observed vedolizumab dataset, using quantile-quantile plots.

Population Pharmacokinetic-Pharmacodynamic Model Development

The population pharmacokinetic-pharmacodynamic analysis for repeated measures was conducted using the nonlinear mixed effects modeling approach (NONMEM, Version 7.2). The pharmacokinetic-pharmacodynamic data were modeled using a sequential approach, where individual predicted vedolizumab serum concentrations from the population pharmacokinetic model were used to drive the pharmacodynamic response. The pharmacodynamic evaluations were based on percentage of MAdCAM-1 binding by lymphocytes expressing high levels of $\alpha_4\beta_7$ integrin ($CD4^+$ $CD45RO^{high}$). A direct effect sigmoid $E_{max}$ model was selected to characterize the exposure-response relationship for the effect of vedolizumab on MAdCAM-1 binding to $\alpha_4\beta_7$. No formal covariate modeling or model evaluation was conducted.

Results

Pharmacokinetic Analysis Population

The study population consisted of 2554 individuals who contributed 18427 evaluable vedolizumab serum samples, including 87 healthy volunteers from the phase 1 study, 46 patients from the phase 2 study (UC), and 891, 1115, and 415 patients from the phase 3 GEMINI 1 (UC), GEMINI 2 (CD), and GEMINI 3 (CD) studies, respectively.

Demographics and other characteristics of the pharmacokinetic analysis population are summarized in Table 1. The analysis population consisted of 1290 men and 1264 women with ages ranging from 18 to 78 years and baseline body weights ranging from 28 to 170 kg. A total of 1530 individuals had CD and 937 had UC; 87 were healthy volunteers.

TABLE 1

Summary of demographics and other characteristics of the pharmacokinetic analysis population (N = 2554)

| Categorical Covariate | n (%) |
|---|---|
| Sex | |
| Women | 1264 (50) |
| Men | 1290 (50) |
| Disease diagnosis | |
| Crohn's disease | 1530 (60) |
| Ulcerative colitis | 937 (37) |
| Healthy volunteers | 87 (3) |
| Mayo Endoscopic Subscore | |
| 1 | 1 (0.039) |
| 2 | 408 (16) |
| 3 | 482 (19) |
| Missing* | 1663 (65) |
| Prior TNF-α antagonist therapy status | |
| Failed | 1321 (52) |
| Naïve | 1100 (43) |
| Missing# | 133 (5) |
| ADA status | |
| Positive (≥1 positive titer) | 124 (5) |
| Negative (no positive titers) | 2430 (95) |

TABLE 1-continued

Summary of demographics and other characteristics of
the pharmacokinetic analysis population (N = 2554)

| Continuous Covariate | n | Median (Range) |
|---|---|---|
| Age, years | 2554 | 36 (18, 78) |
| Body weight, kg | 2554 | 68 (28, 170) |
| Albumin, g/L | 2467 | 37 (11,53) |
| C-reactive protein, mg/L | 1576 | 11 (0.2, 200) |
| Fecal calprotectin, mg/kg | 2421 | 720 (23.75, 20000) |
| CDAI score | 1530 | 320 (93,580) |
| Mayo Score | 891 | 9 (3,12) |
| Partial Mayo Score | 937 | 6 (1,9) |

ADA, anti-drug antibody;
CDAI, Crohn's Disease Activity Index;
TNF-α, tumor necrosis factor-α.
*Data not collected in phase 1 and 2 studies and in GEMINI 2 and 3 studies.
Data not collected in phase 1 and 2 studies.

The median (interquartile range) vedolizumab serum trough concentration-time profiles for patients with UC from GEMINI 1 and patients with CD from GEMINI 2 are shown in FIG. 1.

Population Pharmacokinetic Modeling Results

Base Pharmacokinetic Model

Figure 2:
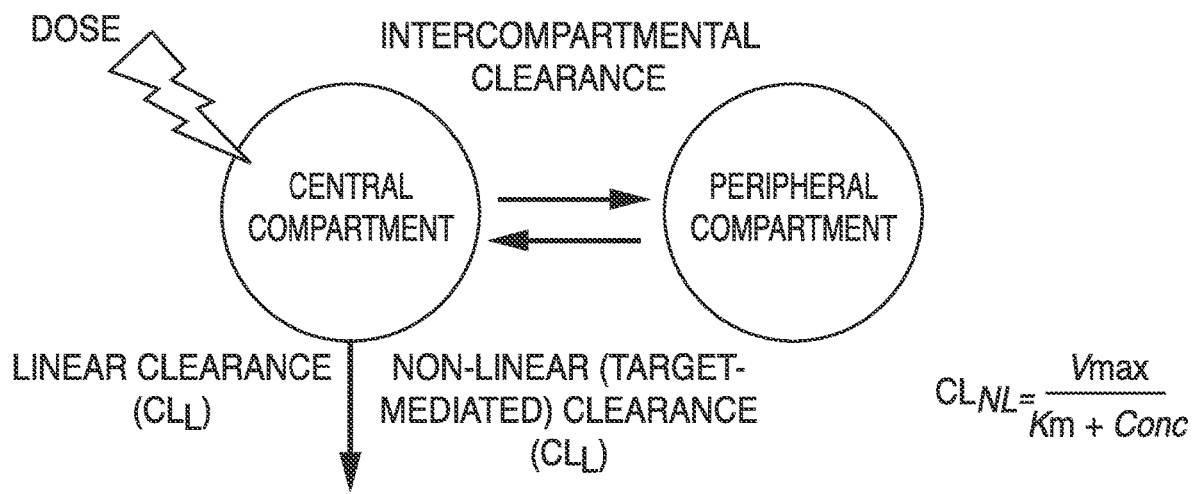
FIG. 2 is a diagramatic representation of the population pharmacokinetic model of vedolizumab. Conc, concentration; $K_m$, Michaelis-Menton constant; $V_{max}$, maximum rate.

Vedolizumab pharmacokinetics was described by a 2-compartment model with parallel linear and nonlinear elimination. A 2-compartment model resulted in a significant improvement in goodness-of-fit criteria over a 1-compartment model, as did a parallel linear and nonlinear elimination model over a linear model. The population pharmacokinetic model of vedolizumab is represented diagrammatically in FIG. 2.

Covariate Pharmacokinetic Model

Strong correlations were identified between the following covariates:body weight~BMI, sex~body weight, CRP~albumin, CRP~fecal calprotectin, CRP~globulin, albumin~globulin, complete Mayo score~partial Mayo score, Mayo endoscopic subscore~complete Mayo score, and Mayo endoscopic subscore~partial Mayo score. Accordingly, sex, CRP, complete Mayo score, Mayo endoscopic subscore, globulin, and BMI were excluded from the full covariate model. The effects of sex, CRP, and endoscopic subscore on the pharmacokinetics of vedolizumab were independently evaluated in an exploratory post hoc fashion once the population pharmacokinetic model was finalized, as described below.

Body weight was chosen to represent changes in vedolizumab pharmacokinetics as a function of body size and was described using an allometric model with a reference weight of 70 kg. The other continuous covariates of albumin, fecal calprotectin, partial Mayo score, age, and CDAI score entered the model as power functions normalized by a reference value (typically near the observed median value of the data). The categorical covariates of prior TNF-α antagonist therapy status, ADA status, concomitant therapy use, and IBD diagnosis entered the model as power functions, with a separate dichotomous (0, 1) covariate serving as an on-off switch for each effect. Time-dependent covariates were body weight, albumin, fecal calprotectin, and concomitant therapy use. The effect of IBD diagnosis on linear clearance ($CL_L$) was investigated by modeling separate $CL_L$ parameters for patients with UC and those with CD, while the effect of IBD diagnosis on central compartment volume of distribution ($V_c$) was evaluated by including IBD as a predictor of $V_c$ in the covariate model.

Final Pharmacokinetic Model Results

The typical pharmacokinetic parameter and variance parameter estimates and 95% CDIs from the final population pharmacokinetic model are shown in Table 2 for the reference covariate values (listed in Table 2 footnotes).

TABLE 2

Parameter estimates from the final population pharmacokinetic model for vedolizumab

| Parameter | Estimate* | Bayesian 95% CDI |
|---|---|---|
| Ulcerative colitis: $CL_L$ | 0.159 L/day | (0.153, 0.165) |
| Crohn's Disease: $CL_L$ | 0.155 L/day | (0.149, 0.161) |
| Central compartment volume of distribution ($V_c$) | 3.19 L | (3.14, 3.25) |
| Peripheral compartment volume of distribution ($V_P$) | 1.65 L | (1.59, 1.71) |
| Intercompartmental clearance (Q) | 0.12 L/day | (0.112, 0.129) |
| Maximum elimination rate ($V_{max}$) | 0.265 mg/day | (0.219, 0.318) |
| Concentration at half-maximum elimination rate ($K_m$) | 0.964 µg/mL | (0.706, 1.27) |
| Proportional residual error variance ($\sigma^2_{prop}$) | 0.0554 (% CV = 23.5) | (0.0539, 0.0568) |

CDI, credible interval;
$CL_L$, clearance of linear elimination pathway;
CV, coefficient of variation.

*Parameter estimate and 95% credible interval were derived from the median, 2.5th and 97.5th quantiles of the Bayesian posterior probability distributions from 4 MCMC chains. Separate typical values of $CL_L$ were modeled for patients with UC and those with CD with a shared inter-individual variance term and shared covariate effects except for partial Mayo score and CDAI score. The reference individual weighs 70 kg, is 40 years old, has an albumin level of 4 g/dL, fecal calprotectin level of 700 mg/kg, CDAI score of 300 (for patient with CD), partial Mayo score of 6 (for patient with UC), ADA negative, a diagnosis of UC (for Vc parameter), and no concomitant therapy use, and is TNF-α antagonist therapy naïve.

Figure 3:
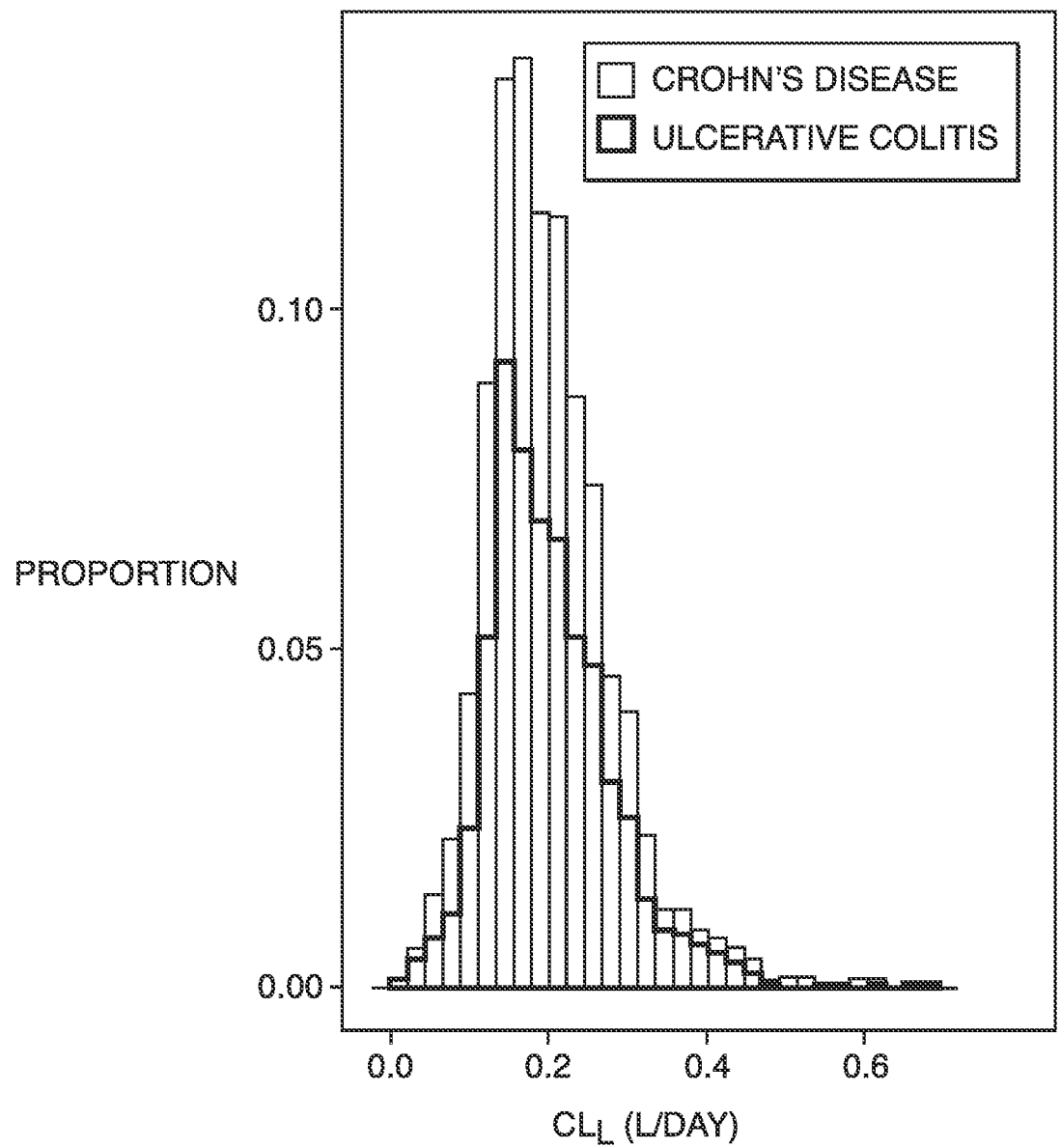
FIG. 3 shows distribution of individual vedolizumab linear clearance ($CL_L$) estimates from the final population pharmacokinetic model in patients with UC and patients with CD.

The pharmacokinetic parameter estimates and overlapping 95% CDIs indicated that $CL_L$ were the same in patients with UC and those with CD. The half-life of vedolizumab for the linear elimination phase was 25.5 days for the typical reference patient and individual estimates ranged from 14.6 to 36.0 days (5th and 95$^{th}$ percentiles). The variance parameter estimates were indicative of moderate to large unexplained interindividual variability. The typical values of $CL_L$ were 0.159 L/day for patients with UC and 0.155 L/day for patients with CD. The individual estimates of $CL_L$ for patients with UC and CD were distributed over a wide range as represented in FIG. 3. The proportional residual variance estimate (unexplained random residual variability in the model) was relatively small. The estimates of interindividual variances and correlations are presented in Table S2, and the standard deviations and shrinkage estimates of interindividual random effects are presented in Table S3.

TABLE S2

Estimates of interindividual variances (% CV) and correlations from the vedolizumab final population pharmacokinetic model

| Parameter | Estimate* | Bayesian 95% Credible Interval* |
|---|---|---|
| $\omega^2_{CLL}$ (% CV) | 34.6 | (33.3, 36.1) |
| $corr_{CLL-Vc}$ | 0.566 | (0.515, 0.615) |
| $\omega^2_{Vc}$ (% CV) | 19.1 | (18.2, 20.1) |
| $corr_{CLL-Vmax}$ | 0.192 | (−0.285, −0.0945) |
| $corr_{Vc-vmax}$ | −0.267 | (−0.378, −0.151) |
| $\omega^2_{Vmax}$ (% CV) | 105 | (94.5, 117) |

TABLE S2-continued

Estimates of interindividual variances (% CV) and correlations from the vedolizumab final population pharmacokinetic model

| Parameter | Estimate* | Bayesian 95% Credible Interval* |
|---|---|---|
| $\omega^2_{Vp}$ (% CV) | 0 Fixed | — |
| $\omega^2_{Q}$ (% CV) | 0 Fixed | — |
| $\omega^2_{Km}$ (% CV) | 0 Fixed | — |

$CL_L$, clearance of linear elimination pathway;
corr, correlation coefficient;
CV, coefficient of variation;
$K_m$, concentration at half-maximum elimination rate;
Q, intercompartmental clearance;
$V_c$, central compartment volume of distribution;
$V_{max}$, maximum elimination rate;
$V_p$, peripheral compartment volume of distribution; o
$\omega^2$, interindividual variance.
*Parameter estimate and 95% credible interval were derived from the median, $2.5^{th}$ and $97.5^{th}$ quantiles of the Bayesian posterior probability distributions from 4 MCMC chains. Separate typical values of $CL_L$ were modeled for patients with UC and those with CD with a shared interindividual variance term and shared covariate effects except for partial Mayo score and CDAI score.

TABLE S3

Standard deviations and shrinkage estimates of interindividual random effects from the vedolizumab final population pharmacokinetic model

| Parameter | SD($\tilde{\eta}$)* | $\omega^{\#}$ | $\eta_{shrink}$ (%) |
|---|---|---|---|
| $ETA_{CLL}$ | 0.329 | 0.346 | 4.85 |
| $ETA_{Vc}$ | 0.156 | 0.191 | 18.5 |
| $ETA_{Vmax}$ | 0.542 | 1.05 | 48.5 |

$CL_L$, clearance of linear elimination pathway;
ETA, interindividual random effect;
SD($\tilde{\eta}$), standard deviation of individual estimates;
$V_c$, central compartment volume of distribution;
$V_{max}$, maximum elimination rate;
$\omega$, standard deviation of variance estimate;
$\eta_{shrink}$ (%) = 100 · (1 − SD($\eta$)/$\omega$).
*Individual estimate used for the calculation SD($\eta$) was derived as the median of the individual's random effect estimates from 4 MCMC chains.
$^{\#}\omega$ estimate was derived from the median of the Bayesian posterior probability distributions from 4 MCMC chains.

Figure 4:
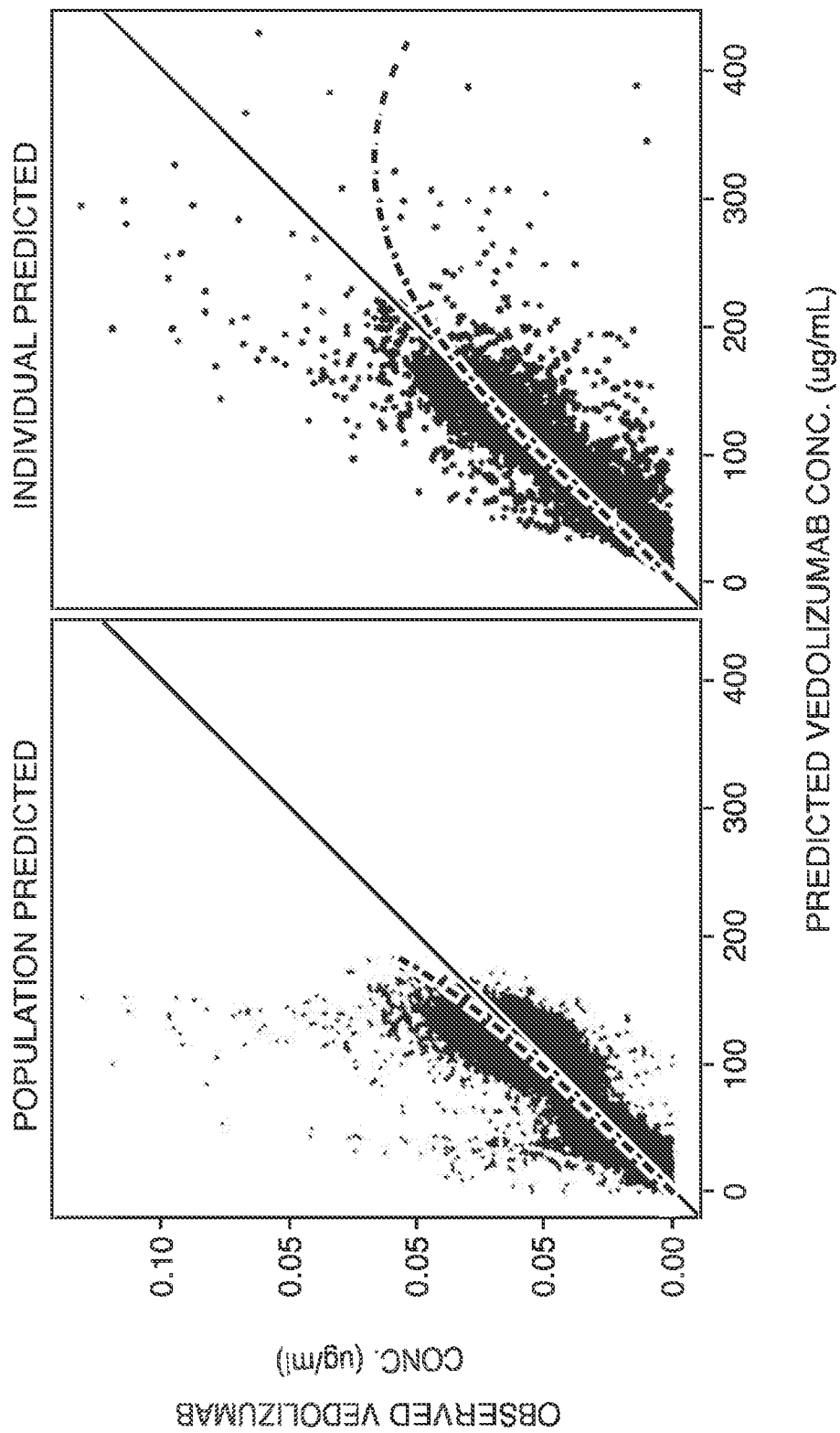
FIG. 4 is a goodness-of-fit plot: observed vedolizumab concentration versus predicted vedolizumab concentration from the final population pharmacokinetic model. Values are indicated by closed circles with a dashed black loss trend line through the data. The line of identity (solid white) is included as reference.
Figure 5:
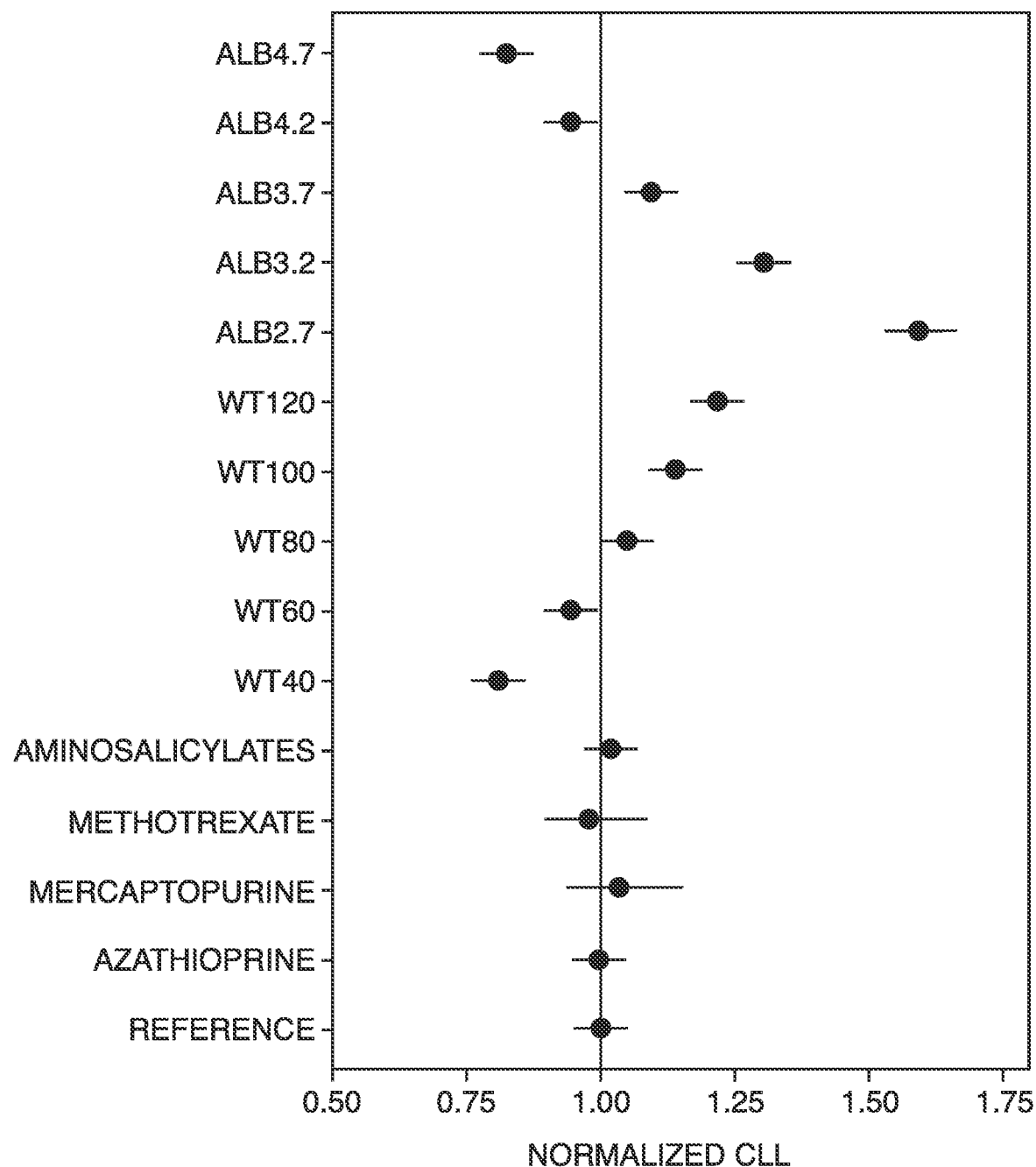
FIG. 5 shows the effect of covariates on vedolizumab linear clearance ($CL_L$). Each point and line represents the median and 95% credible interval (CDI), respectively, of the Bayesian posterior distribution of normalized samples of vedolizumab $CL_L$ adjusted for the covariate. The reference individual weighs 70 kg, is 40 years old, has an albumin level of 4 g/dL, fecal calprotectin level of 700 mg/kg, CDAI score of 300 (for patient with CD), partial Mayo score of 6 (for patient with UC), ADA negative, and no concomitant therapy use, and is TNF-α antagonist therapy naïve. Albumin: 2.7, 3.2, 3.7, 4.0, 4.2, and 4.7 g/dL represent the 6th, 18th, 50th, 70th, 85th, and 98.5th percentiles, respectively, of baseline albumin levels for patients in GEMINI 1, 2, and 3. Weight: 40, 60, 80, 100, and 120 kg represent the 1.5th, 30th, 71st, 92nd, and 98th percentiles, respectively, of baseline weight values for patients in GEMINI 1, 2, and 3. The vertical black line is drawn at the reference point estimate, and the shaded region is ±25% of the reference point estimate chosen to represent an uncertainty range of clinical unimportance.
Figure 9:
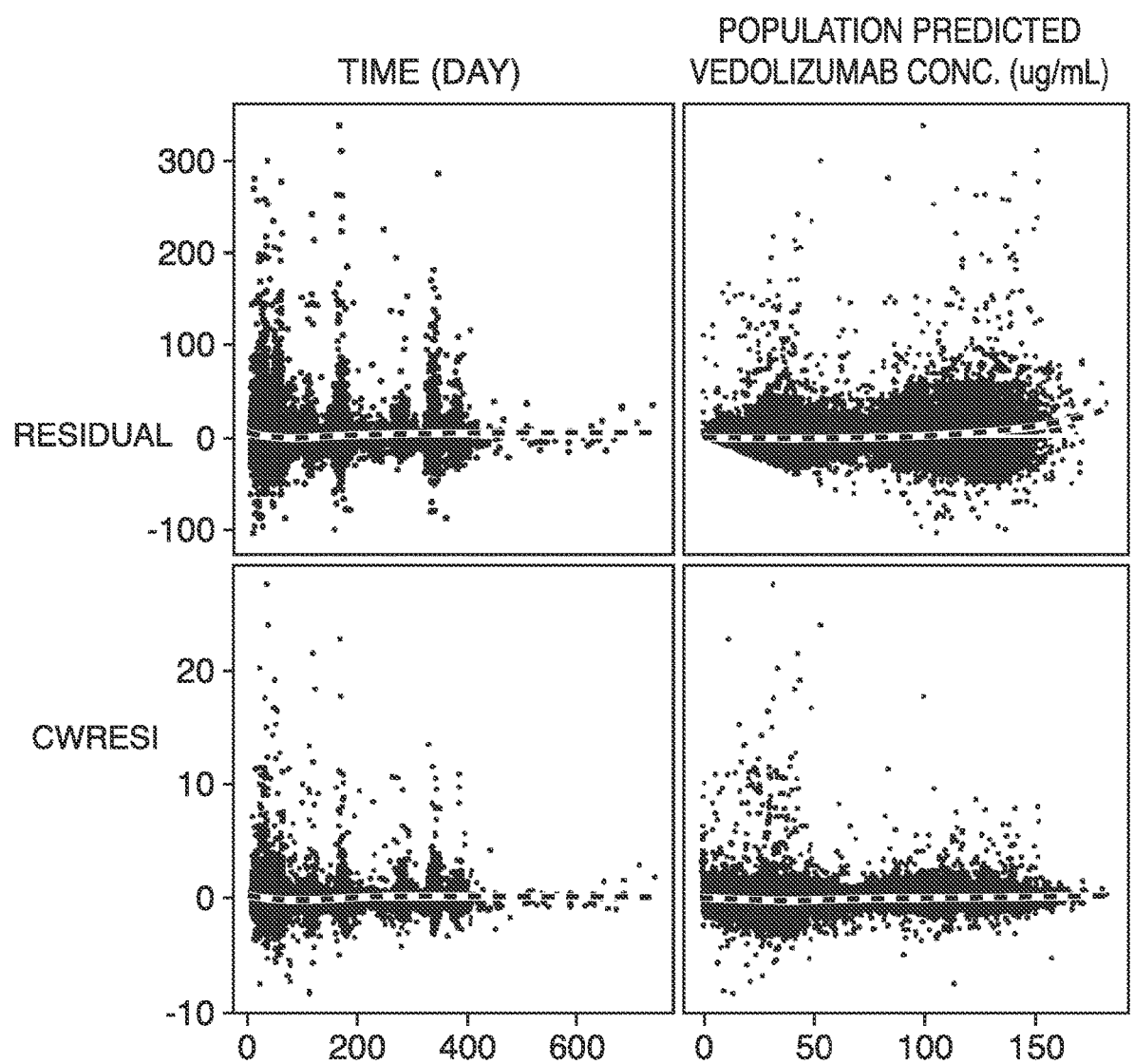
FIG. 9 is a goodness-of-fit plot for the vedolizumab final population pharmacokinetic model: CWRESI and residual versus time and population predicted vedolizumab concentration.

Goodness-of-fit plots from the final population pharmacokinetic model are presented in FIGS. 4 and 9. Diagnostic plots indicated that the full covariate pharmacokinetic model was consistent with the observed data and no systematic bias was evident. The relative changes in $CL_L$ for a reference individual with various covariate values are illustrated in FIG. 5. The point estimates and 95% CDIs for the effects of covariates on $CL_L$ are presented in Table S4.

TABLE S4

Covariate parameter estimates from the vedolizumab final population pharmacokinetic model

| Parameter | Estimate* | Bayesian 95% Credible Interval* |
|---|---|---|
| Continuous covariates effects (NULL effect = 0) | | |
| Weight on $CL_L$ | 0.362 | (0.299, 0.427) |
| Albumin on $CL_L$ | −1.18 | (−1.24, −1.13) |
| Fecal calprotectin on $CL_L$ | 0.0310 | (0.0252, 0.0358) |
| CDAI score on $CL_L$ | −0.0515 | (−0.14, 0.0358) |
| Partial Mayo score on $CL_L$ | 0.0408 | (−0.0336, 0.115) |
| Age on $CL_L$ | −0.0346 | (−0.0788, 0.01) |
| Weight on $V_c$ | 0.467 | (0.423, 0.511) |
| Weight on $V_P$ | 1 Fixed | (1, 1) |
| Weight on $V_{max}$ | 0.75 Fixed | (0.75, 0.75) |
| Weight on Q | 0.75 Fixed | (0.75, 0.72) |

TABLE S4-continued

Covariate parameter estimates from the vedolizumab final population pharmacokinetic model

| Parameter | Estimate* | Bayesian 95% Credible Interval* |
|---|---|---|
| Categorical covariates effects (NULL effect = 1) | | |
| Prior TNF-α antagonist therapy status on $CL_L$ | 1.04 | (1.01, 1.07) |
| ADA status on $CL_L$ | 1.12 | (1.05, 1.2) |
| AZA on $CL_L$ | 0.998 | (0.964, 1.03) |
| MP on $CL_L$ | 1.04 | (0.943, 1.15) |
| MTX on $CL_L$ | 0.983 | (0.899, 1.07) |
| AMINO on $CL_L$ | 1.02 | (0.988, 1.05) |
| IBD diagnosis on $V_c$ | 1.01 | (0.989, 1.03) |

AMINO, aminosalicylate concomitant therapy;
AZA, azathioprine concomitant therapy;
CD, Crohn's Disease;
CDAI, Crohn's disease activity index;
$CL_L$, clearance of linear elimination pathway;
ADA, anti-drug antibody;
MP, 6-mercaptopurine concomitant therapy;
MTX, methotrexate concomitant therapy;
Q, intercompartmental clearance;
TNF-α, tumor necrosis factor-α;
UC, ulcerative colitis;
$V_c$, central compartment volume of distribution;
$V_{max}$, maximum elimination rate;
$V_p$, peripheral compartment volume of distribution.
*Parameter estimate and 95% credible interval were derived from the median, $2.5^{th}$ and $97.5^{th}$ quantiles of the Bayesian posterior probability distributions from 4 MCMC chains. Separate typical values of $CL_L$ were modeled for patients with UC and those with CD with a shared interindividual variance term and shared covariate effects except for partial Mayo score and CDM score. The reference individual weighs 70 kg, is 40 years old, has an albumin level of 4 g/dL, fecal calprotectin level of 700 mg/kg, CDAI score of 300 (for patient with CD), partial Mayo score of 6 (for patient with UC), ADA negative, a diagnosis of UC (for Vc parameter), and no concomitant therapy use, and is TNF-α antagonist therapy naive In general, the 95% CDIs were narrow indicating that the effect of each covariate on vedolizumab $CL_L$ was well defined. Only the effects of albumin and body weight had potential to be clinically meaningful (effect sizes greater than 25%) at extremes values of a representative range. The typical $CL_L$ values for patients with albumin levels of 4.7 and 3.2 g/dL were approximately 0.8 and 1.3 times, respectively, that of the reference patient (albumin, 4 g/dL) (FIG. 5). The typical $CL_L$ value for a patient of 40 kg was approximately 0.8 times that of the reference patient (weight, 70 kg). At the other end of the body weight range, a patient of 120 kg had 1.2 times higher $CL_L$ than the reference patient (FIG. 5). A patient of 120 kg with a serum albumin concentration of 4.0 g/dL had a 19% probability of having clearance greater than the pre-specified criterion for clinical significance. When evaluated across a representative range of covariate values and categories, the effects of fecal calprotectin, CDAI score, partial Mayo score, age, prior TNF-α antagonist therapy status, ADA status, and concomitant therapy use on vedolizumab $CL_L$ were not considered clinically relevant since the covariate effect sizes were less than ±25% from the typical reference values (Table S4). In addition, the 95% CDIs for these covariate effects were generally narrow and contained the null effect value.

The final population pharmacokinetic model was rerun with all covariates and pharmacokinetic parameters fixed to estimates from the final model (interindividual variances were re-estimated), and any remaining effects of sex on $CL_L$ and $V_c$ were quantified. The results of this analysis suggest that, after adjusting for other predictors of vedolizumab pharmacokinetics, the typical $CL_L$ value and $V_c$ are approximately 10% lower and 6% lower, respectively, for a female patient compared with a male patient. However, these effects were not considered clinically relevant since the covariate effect sizes were less than ±25% from the typical reference values (male patient). Addition of the sex effect explained approximately 4.2% and 6.0% of the unexplained interindividual variability in $CL_L$ and $V_c$, respectively.

The final population pharmacokinetic model also was re-run to estimate any remaining effect of CRP on $CL_L$. The results suggest that, after adjusting for other predictors of vedolizumab pharmacokinetics, the effect of CRP on $CL_L$ was not clinically relevant since the covariate effect size was less than ±25% from the typical reference value (CRP, 11 mg/dL) when evaluated over a range of baseline CRP values of 0.46 to 93 mg/dL (observed $2.5^{th}$ and $97.5^{th}$ percentiles). The addition of the CRP effect explained <1% of the unexplained interindividual variability in $CL_L$.

Figure 6:
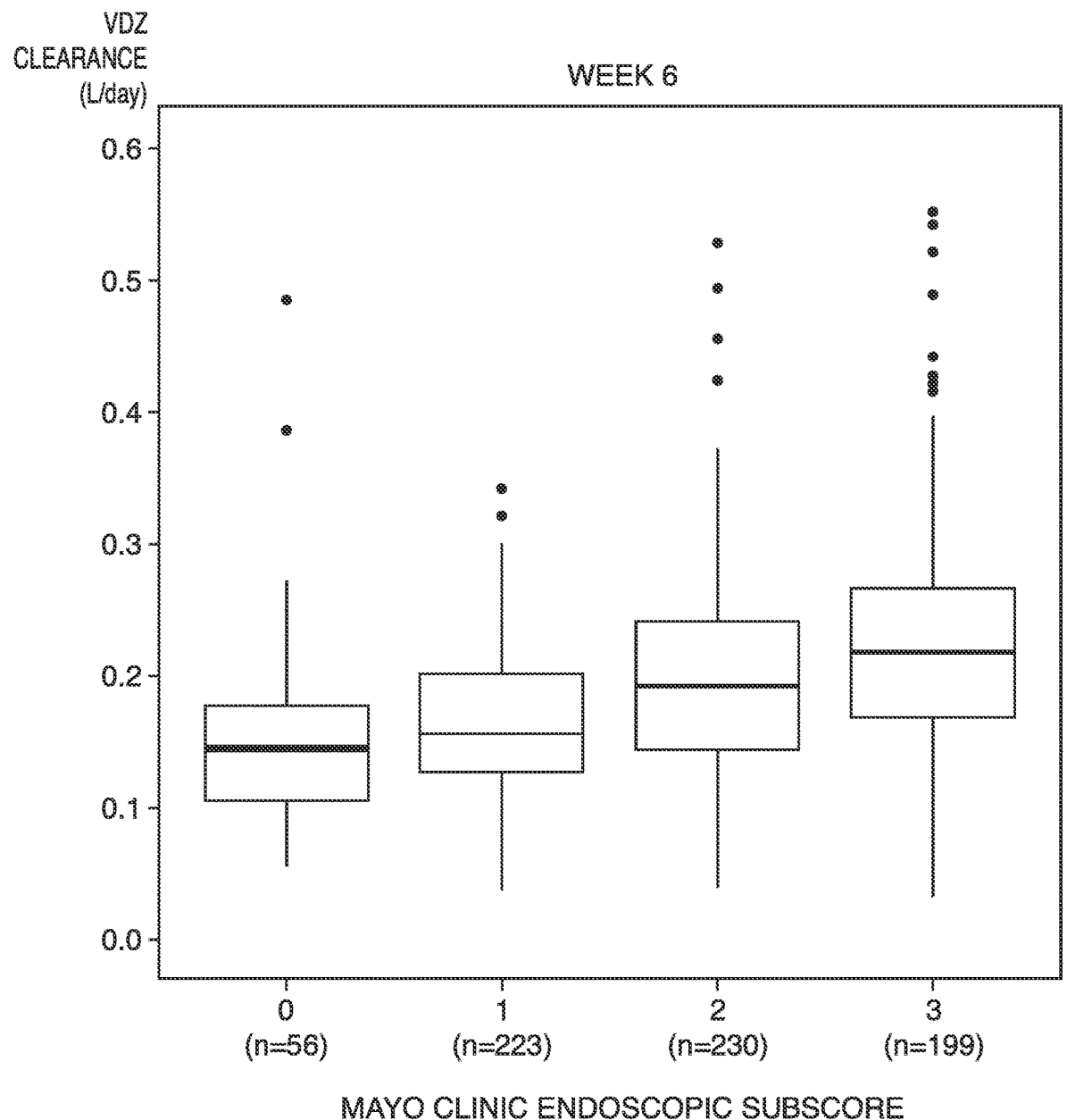
FIG. 6 shows individual vedolizumab linear clearance ($CL_L$) estimates at the end of induction (week 6) by Mayo clinic endoscopic subscore for patients with UC (GEMINI 1). Midlines represent medians. Box limits represent 25th and 75th percentiles. Whiskers (error bars) represent highest and lowest points within 1.5×interquartile range. Individual points represent outliers.

For patients with UC, the effect of Mayo endoscopic subscore was evaluated graphically by plotting individual estimates of CIA, from the final population pharmacokinetic model by endoscopic subscores at week 6 (FIG. 6). From this analysis, at week 6 (end of induction treatment), patients with an endoscopic subscore of 3 have on average 25% higher $CL_L$ than patients with an endoscopic subscore of 0.

Pharmacokinetic Model Evaluation

Figure 10:
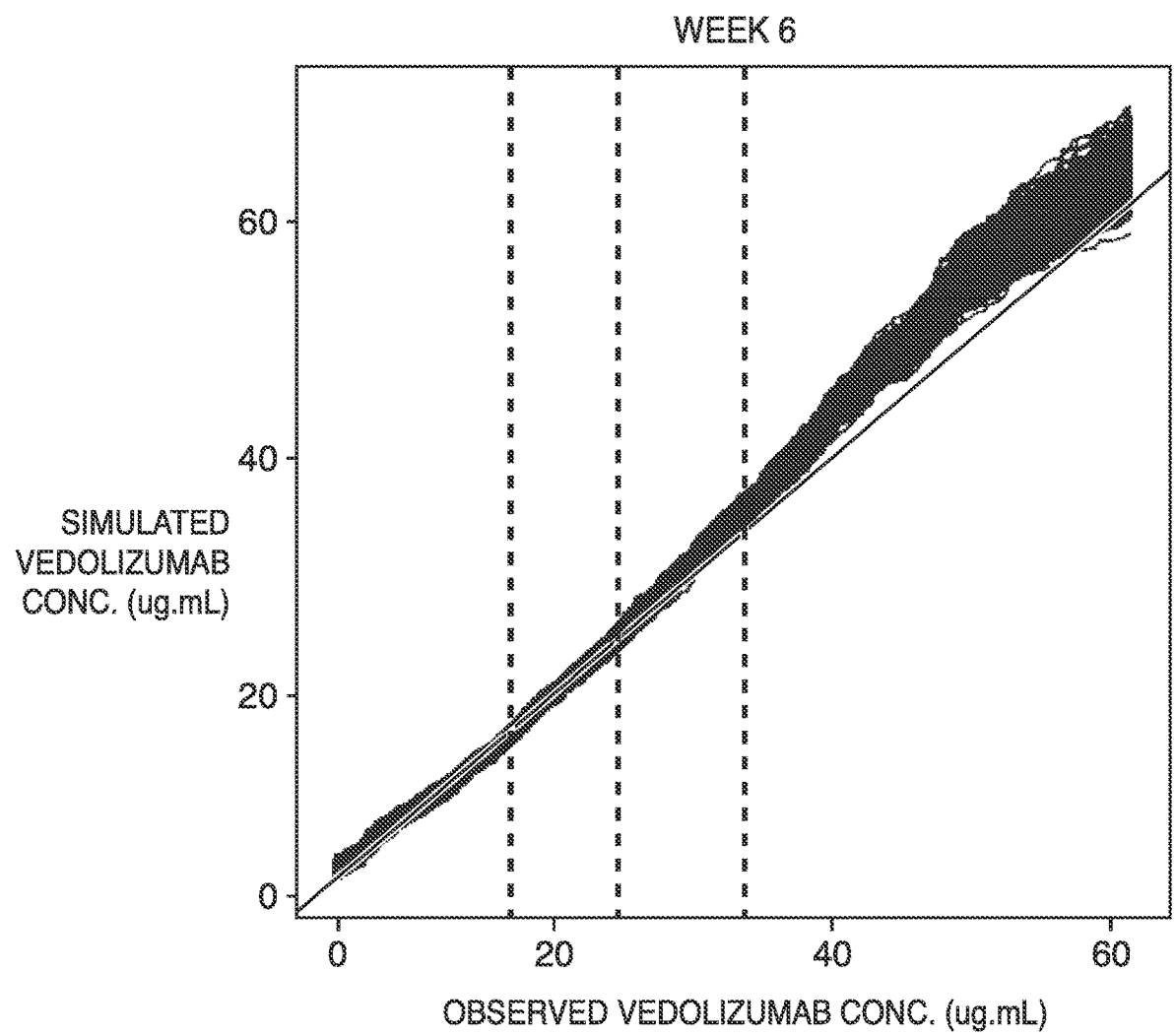
FIG. 10 shows a predictive check for the vedolizumab final population pharmacokinetic model: induction therapy.
Figure 11:
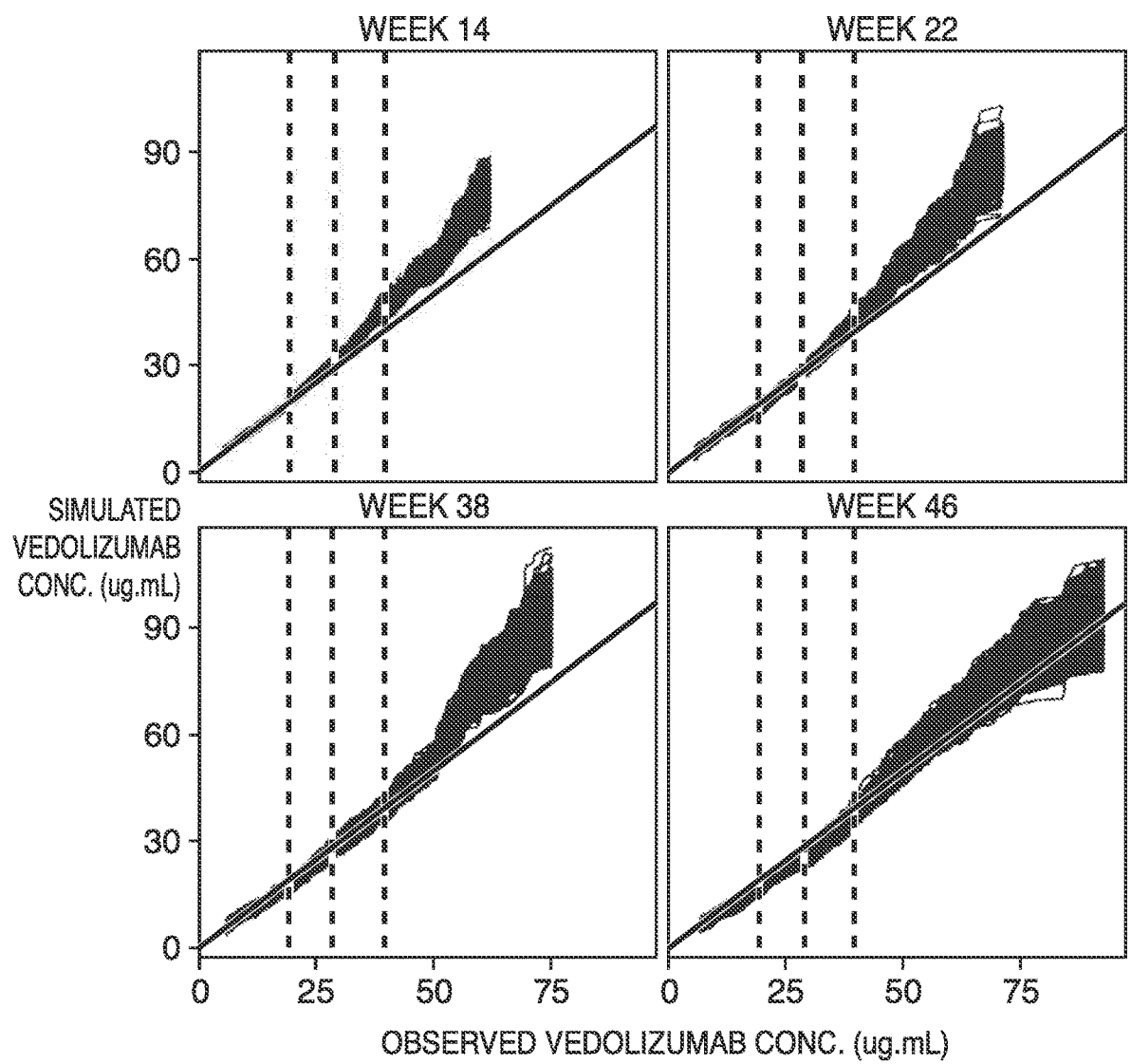
FIG. 11 shows a predictive check for the vedolizumab final population pharmacokinetic model: maintenance therapy—every 4 weeks.
Figure 12:
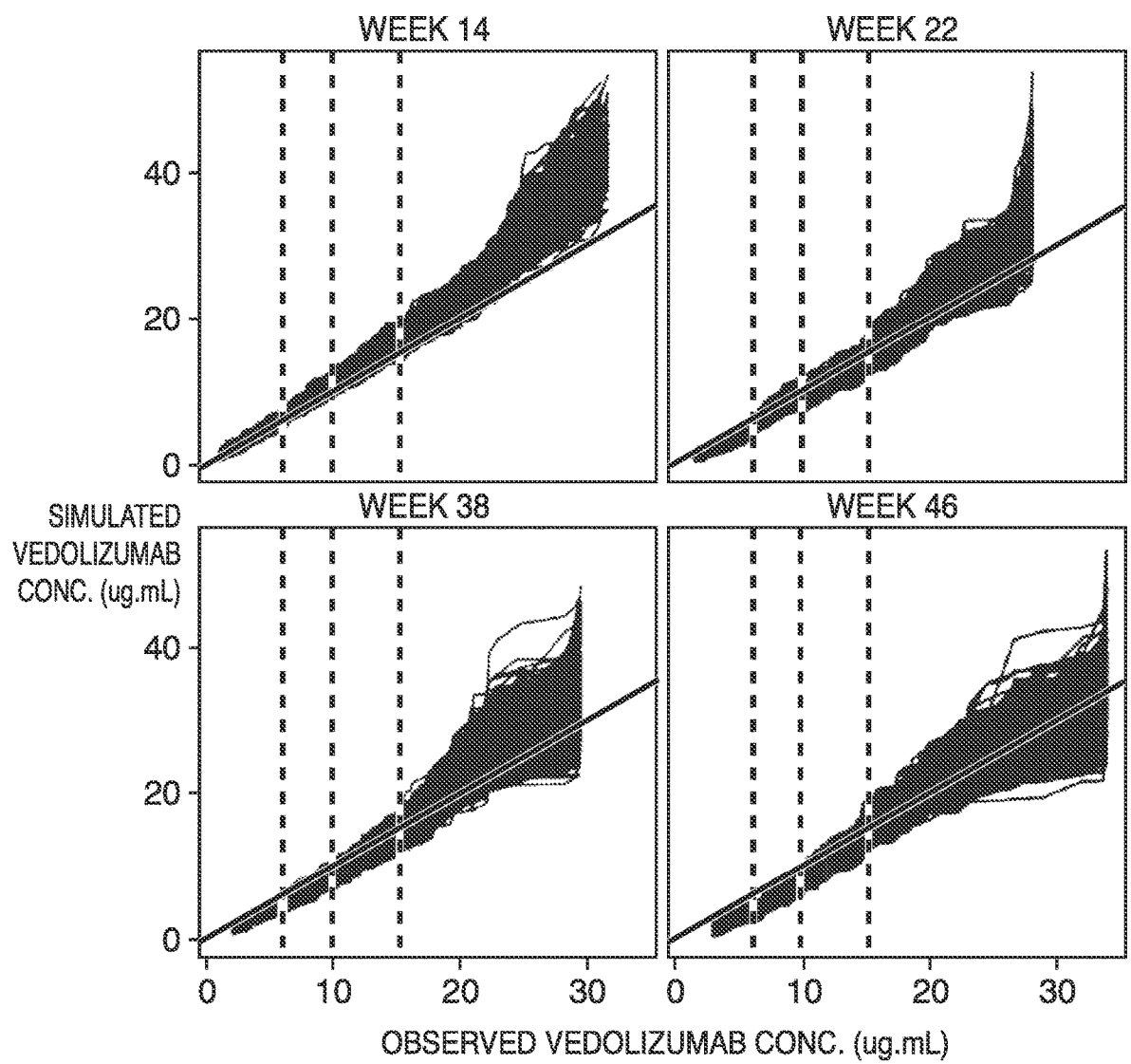
FIG. 12 is a predictive check for the vedolizumab final population pharmacokinetic model: maintenance therapy—every 8 weeks.

The final population pharmacokinetic model and parameter estimates were evaluated with a predictive check method and Bayesian 95% CDIs derived from the posterior probability distributions. The basic premise of a predictive check is that a model and parameters derived from an observed dataset should produce simulated data that are similar to the original observed data. The predictive check plots demonstrated overall good agreement between the observed and simulated data (FIGS. 10, 11, and 12). The precision of the parameters estimates was assessed by evaluating the Bayesian 95% CDIs (Tables 2, S2, and S4). Overall, the structural pharmacokinetic model parameters, covariates effects, and variance parameters were estimated with good precision.

Pharmacokinetic-Pharmacodynamic Analysis Population

The vedolizumab population pharmacokinetic-pharmacodynamic dataset was composed of 593 individuals contributing a total of 2442 evaluable MAdCAM-1 observations. The analysis population consisted of 297 patients with UC and 296 patients with CD (from the phase 2 study and GEMINI 1 and 2).

Figure 7:
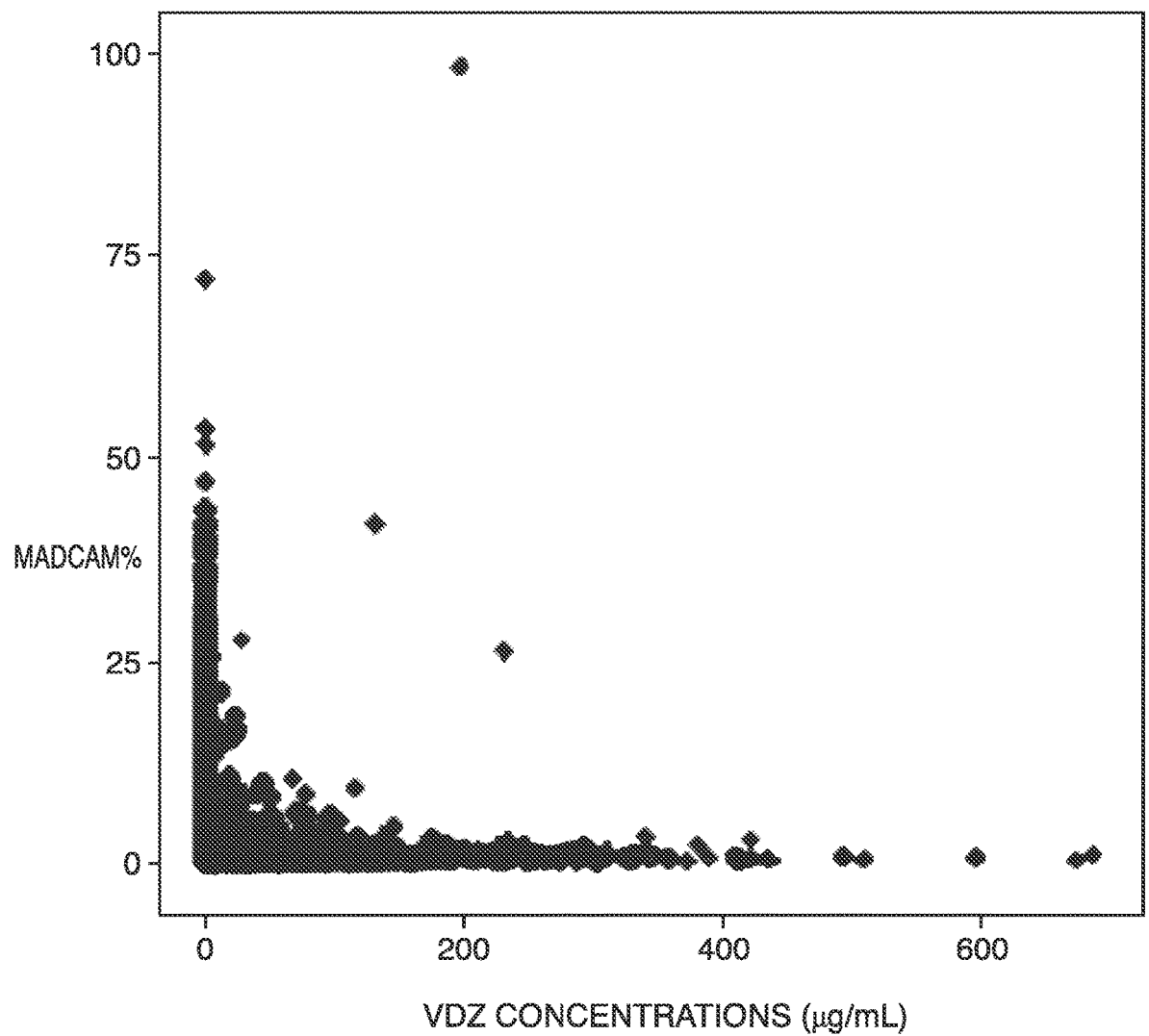
FIG. 7 is a receptor ($\alpha_4\beta_7$) saturation plot: observed MAdCAM-1 versus observed vedolizumab concentration in patients with UC (GEMINI 1) and patients with CD (GEMINI 2). Baseline data are excluded.
Figure 8:
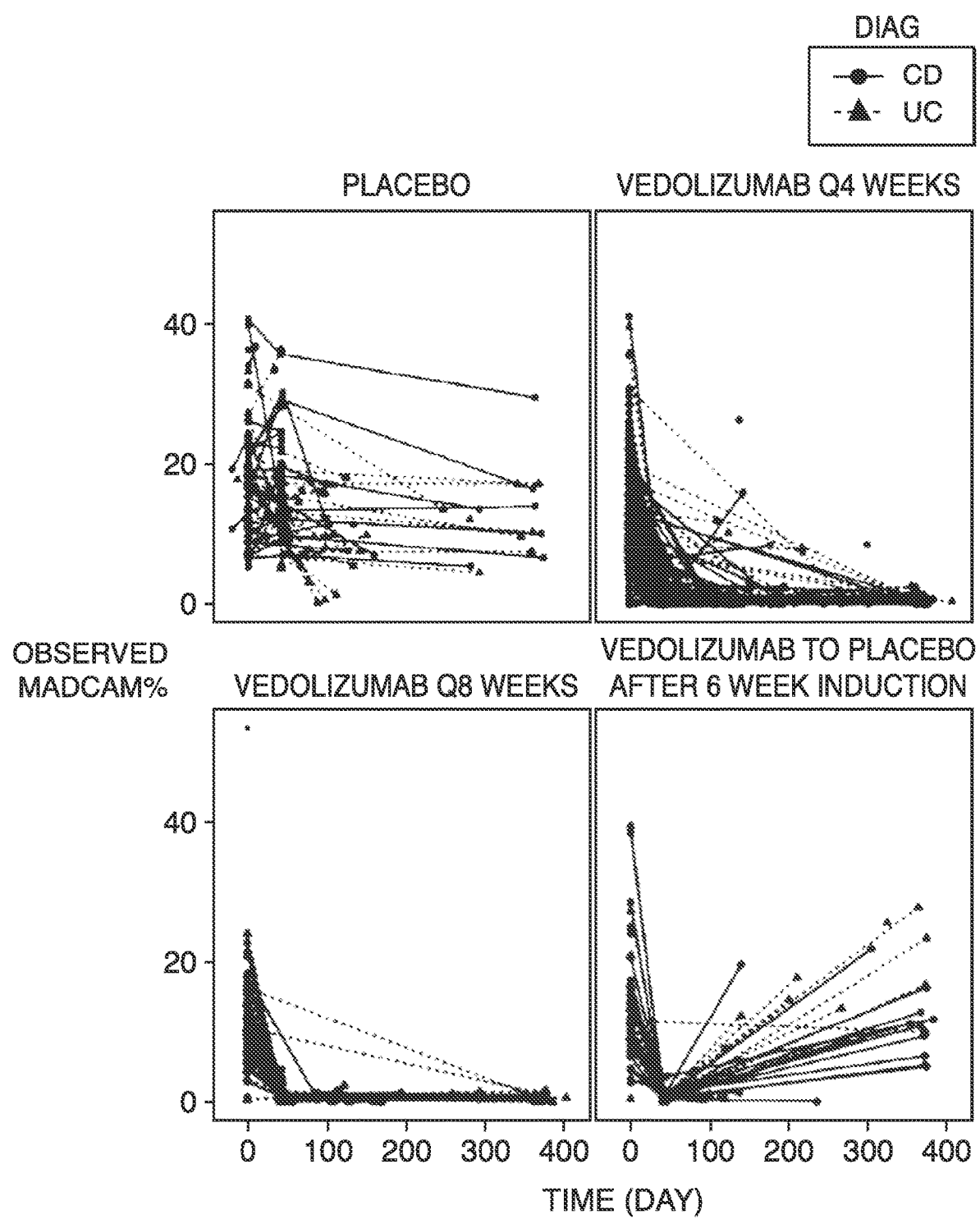
FIG. 8 shows observed MAdCAM-1 versus time for patients with UC (GEMINI 1) and patients with CD (GEMINI 2).

During the analysis, the log-transformed values of MAdCAM-1 (free $α_4β_7$ receptors not blocked by vedolizumab) were modeled. A plot of observed MAdCAM-1 measurements (percentage of free $α_4β_7$ receptors) versus observed vedolizumab serum concentrations for patients with UC and CD from GEMINI 1 and 2 is presented in FIG. 7. Plots of observed MAdCAM-1 measurements versus time by treatment regimen for patients with UC and CD in GEMINI 1 and 2 are presented in FIG. 8. The percentage of free $α_4β_7$ receptors declined rapidly after the first dose and was maintained during repeated IV infusions of vedolizumab 300 mg.

Pharmacokinetic-Pharmacodynamic Modeling Results

A direct effect sigmoid $E_{max}$ model was chosen as the structural model to describe the pharmacokinetic-pharmacodynamic relationship of vedolizumab as follows:

$$MAdCAM - 1 = E_0 * \left(1 - \frac{E_{max} * Conc^\gamma}{EC_{50} + Conc^\gamma}\right)$$

where Eo is the baseline MAdCAM-1 percent binding, Emax is the maximum effect, Conc is the vedolizumab serum concentration, EC50 is the vedolizumab serum concentration at half-maximum effect, and γ is the Hill-coefficient or slope factor.

The model was parameterized in terms of baseline MAdCAM-1 inhibition ($E_0$), maximum effect ($E_{max}$), vedolizumab serum concentration at half-maximum effect ($EC_{50}$), and Hill-coefficient or slope factor (γ). The structural parameter estimates are presented in Table 3 and were estimated with adequate precision. An attempt was made to model a placebo effect, but the estimated effect was negligible. The lack of an apparent effect was consistent with the observed MAdCAM-1 data in placebo-treated patients.

TABLE 3

Parameter estimates from base MAdCAM-1 population pharmacokinetic-pharmacodynamic model for vedolizumab

| Parameter | Estimate | Percent Relative Standard Error |
|---|---|---|
| Baseline MAdCAM-1 inhibition ($E_0$) | 12.1% | 3.49 |
| Concentration at half maximum effect ($EC_{50}$) | 0.093 µg/mL | 25.8 |
| Maximum effect ($E_{max}$) | 0.959 | 0.503 |
| Hill-coefficient or slope factor (γ) | 0.801 | 11.1 |
| Exponential residual error variance ($\sigma^2_{exp}$) | 0.613 (% CV = 78.3) | 10.4 |

CV, coefficient of variation.

Figure 13:
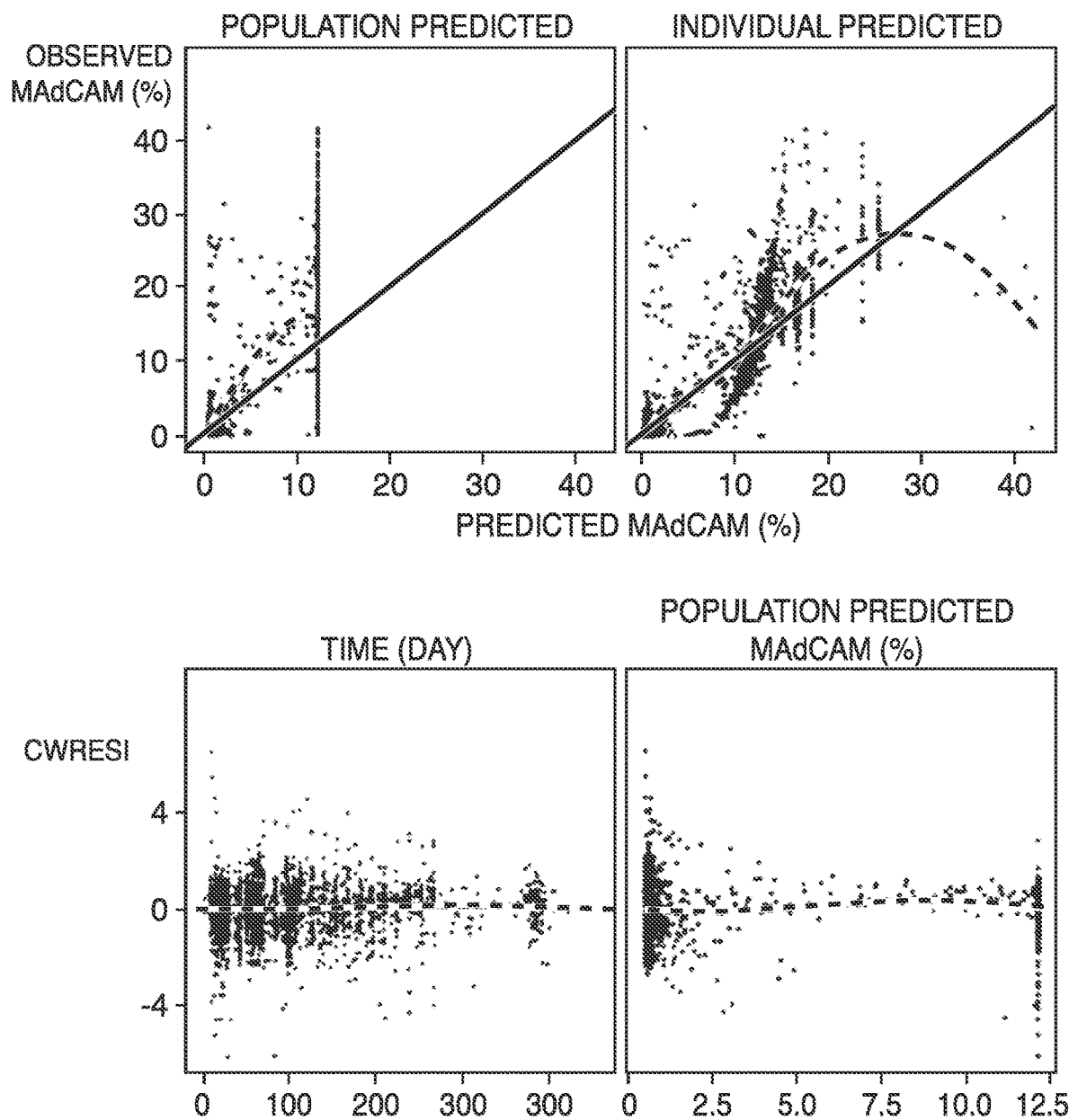
FIG. 13 is a goodness-of-fit model for MAdCAM-1.

The base model provided a reasonable description of the data as judged by visual inspection of diagnostic plots (FIG. 13) but some deficiencies in the model were noted. Variance parameter estimates were indicative of moderate to large unexplained interindividual and residual variability, with estimates of 41.8% CV for $E_0$, 0.551 (SD logistic distribution) for $E_{max}$, and 78.3% CV for the exponential residual error variance ($\sigma^2_{exp}$) (Table 3).

Discussion

We developed a population pharmacokinetic model for vedolizumab following IV administration to healthy volunteers and patients with UC and CD using data collected in clinical trials with identical designs and sampling schedules. These design features allowed the direct comparison of the disposition and the pharmacokinetic variability of vedolizumab in patients with UC and those in patients with CD. The estimated half-life of vedolizumab was not different between the 2 diseases and was 25.5 days (range 14.6-36.0 days [$5^{th}$ and $95^{th}$ percentiles]), which is typical of human $IgG_1$ (25 days) and typical of monoclonal antibodies of the $IgG_1$ type A2. This half-life is substantially longer than values for current biologic treatments for IBD. Clinicians should be aware of the relatively long half-life of vedolizumab in circumstances when it is desirable to minimize exposure to the drug. Relevant examples include patients who develop an enteric infection during treatment and women who become pregnant and receive drug within the third trimester.

A 2-compartment pharmacokinetic model consisting of parallel clearance via the nonlinear pathway ($CL_{NL}$) and the linear pathway ($CL_L$) from the central compartment was selected as the base model. The nonlinear elimination was best described by Michaelis-Menten elimination. Physiologically, the nonlinear pathway is thought to be due to clearance by saturable, target-mediated mechanisms such as receptor-mediated endocytosis. In contrast, the linear pathway represents components that are non-saturable at therapeutic concentrations, such as Fc-mediated elimination. Parallel elimination is typical of monoclonal antibodies with disposition that is affected by binding to the target, in this case the $\alpha_4\beta_7$ integrin on circulating T lymphocytes. Similar effects have been reported for efalizumab, tocilizumab, and cetuximab. In contrast, the elimination of TNF-α antagonists is best described by a linear elimination process. After IV administration, the elimination of infliximab in patients with UC or ankylosing spondylitis and of golimumab in patients with rheumatoid arthritis follows a 2-compartment model with linear elimination. TNF-α exists in both soluble and membrane-bound forms and is present in abnormally high concentrations in serum and gut mucosa in patients with IBD. The localization of TNF-α in inflammatory tissues may make it difficult to rapidly achieve target saturation because of slow redistribution of the drug from plasma to the target sites. Accordingly, it may be difficult to achieve target saturation at therapeutic concentrations. Furthermore, variability in TNF-α concentrations in different compartments results in drug redistribution, with possible effects on pharmacokinetic and pharmacokinetic-efficacy/safety relationships of TNF-α antagonists. The clinical implications of these differences in elimination pathways are not currently understood.

The estimated vedolizumab $CL_L$ values are consistent with those of other monoclonal antibodies that are administered intravenously. Although some authors have reported that the clearance of antibodies could be affected by IBD type, no apparent differences were observed in the pharmacokinetics of vedolizumab in patients with UC and those with CD. Results from the final pharmacokinetic model showed that vedolizumab $CL_L$ for a 40-year-old, 70-kg patient with a serum albumin concentration of 4 g/dL was 0.159 L/day for a patient with UC and 0.155 L/day for a patient with CD.

We evaluated the potential effects of intrinsic and extrinsic covariates (body weight, age, albumin, fecal calprotectin, CDAI score, partial Mayo score, concomitant therapy use, AVA status, and prior TNF-α antagonist therapy status) on vedolizumab $CL_L$. Extreme values of albumin and weight had important effects on drug clearance. Specifically, clearance increased as albumin concentrations decreased and weight increased. Albumin concentrations below 3.2 g/dL, for a patient of 70 kg, were associated with increased clearance of vedolizumab that was greater than the pre-specified criterion for clinical significance. Similar association of low albumin concentrations with the clearance of other monoclonal antibodies have been reported in population pharmacokinetics analyses. Although the mechanism of this interaction is incompletely understood, the Fc receptor (FcRn), which is expressed in a wide variety of cells and tissues throughout the body, including the vascular endothelium, monocytes, macrophages, dendritic cells, hepatocytes, and epithelial cells of the intestine, renal proximal convoluted tubules, and upper airways, facilitates IgG and albumin homeostasis by salvaging these molecules from proteolysis and recycling them into the central circulatory system. It has been postulated that decreased expression and/or activity of FcRn results in low albumin concentrations as a result of less efficient salvage of IgGs, including therapeutic antibodies, and albumin; the net result is increased antibody clearance and in this case lower serum vedolizumab concentrations. However, this hypothesis has not been proven. Another explanation might be that inflammation of the digestive tract in patient with IBD can result in an unconventional route of elimination. Specifically, in the setting of severe colitis, patients may develop a protein-losing colopathy in which large amounts of protein are lost from the luminal surface. Albumin may therefore serve as a surrogate marker for loss of endogenous IgG and monoclonal antibodies via this pathway. Support for this hypothesis comes from observations in patients with severe colitis treated with infliximab in which high concentrations of the monoclonal antibody were identified in the stool. Conversely, serum drug concentrations were low in these patients. Successful treatment was associated with resolution of this phenomenon. Vedolizumab concentrations in feces were not measured during the GEMINI trials precluding us from evaluating this hypothesis.

The second important covariate identified was body weight, which was positively correlated with the clearance of vedolizumab. A patient of 120 kg with a serum albumin concentration of 4.0 g/dL had a 19% probability of having clearance greater than the pre-specified criterion for clinical significance. Measures of body size are the most commonly identified covariates influencing the pharmacokinetics of therapeutic monoclonal antibodies. The impact of body weight on vedolizumab pharmacokinetics is consistent with that reported in population analyses of other therapeutic monoclonal antibodies.

Other potential covariates had lesser effects on vedolizumab clearance than weight and albumin. Intensity of inflammation has been identified as a predictor of high drug clearance for other monoclonal antibodies. In our analyses, patients with UC with lower Mayo endoscopic subscores had on average lower clearance than patients with higher endoscopic subscores. However, these results should be interpreted with caution since higher TNF-α antagonist trough levels have been reported in patients with UC and CD with mucosal healing, which raises the possibility that this relationship is not causal and merely reflects the association between drug-losing enteropathy, mucosal healing, and albumin concentrations.

Intensity of inflammation has been reported as a positive predictor of clearance for other monoclonal antibodies. A post hoc exploratory analysis estimated the effect of CRP as a predictor of unexplained random variability in vedolizumab clearance after accounting for effects of other covariates present in the existing final population pharmacokinetic model (such as albumin). These results suggest that the effect of CRP on $CL_L$ is not clinically relevant and explained less than 1% of the unexplained interindividual variability in vedolizumab $CL_L$. In contrast, high CRP concentrations are strongly associated with increased clearance of anti-TNF-α monoclonal antibodies. Therefore, as albumin and CRP were strongly correlated, any potential effect of CRP on vedolizumab $CL_L$ was already accounted for in the model by incorporating albumin.

The development of ADAs has been reported to increase infliximab clearance. In the current analysis, the presence of ADAs was estimated to increase vedolizumab clearance by only 12%. The small impact may be a result of the low incidence of ADAs observed in the GEMINI trials. However, in the few patients who were persistently positive for ADAs in these studies, vedolizumab trough concentrations were below the limit of quantification. We believe that sensitization of patients to monoclonal antibodies is an important cause of treatment failure and that vedolizumab is not unique in this regard.

The current population pharmacokinetic analysis showed no clinically meaningful impact of the following covariates on the pharmacokinetics of vedolizumab: disease activity, prior TNF-α antagonist therapy status, age (from 18 to 78 years old), and concomitant medication use. The lack of association between prior TNF-α antagonist therapy use was associated with a higher probability of clinical remission or response in vedolizumab-treated patients with UC and those with CD. Taken together, these observations suggest that the impact of prior TNF-α antagonist therapy use on vedolizumab efficacy is not related to any effect on vedolizumab $CL_L$.

The lack of an effect of thiopurines and methotrexate on the pharmacokinetics of vedolizumab differs from TNF-α antagonists in both IBD and rheumatoid arthritis patients where co-administration of these agents is associated with higher trough concentrations and lower drug clearance. The mechanism by which antimetabolites increase concentrations of biologic drugs is not well understood, however, modulation of Fcγ expression is one possible explanation. For example, methotrexate is known to down-regulate Fcγ receptors on monocytes and other Fc-receptor subtypes. Furthermore, prevention of the ADA development increases drug exposure by reducing immune-mediated drug clearance. The reason behind the lack of effect of concomitant medications on vedolizumab $CL_L$ is not currently understood. A sensitivity analysis was performed to determine whether the rate of concomitant medication use in the vedolizumab population pharmacokinetic data set was sufficient to achieve at least 80% power to detect no drug interaction, as recommended by the Population Pharmacokinetic Therapeutic Protein-Drug Interaction (PK TPDI) Working Group. This analysis revealed that the data set met the sample size requirements to ensure at least 80% power and confirmed that vedolizumab $CL_L$ was not impacted by concomitant use of azathioprine, mercaptopurine, methotrexate or aminosalicylates.

Interestingly, α4β7 receptor saturation was maintained at vedolizumab concentrations considered subtherapeutic, raising the question as to whether receptor saturation is necessary but not sufficient for clinical efficacy. The $EC_{50}$ estimate from population pharmacokinetic-pharmacodynamic model was 0.093 µg/mL, suggesting that full saturation is reached at vedolizumab serum concentration of approximately 1 µg/mL. The exposure-efficacy results indicated that vedolizumab concentrations below 17 and 15 µg/mL at induction were associated with efficacy similar to placebo in patients with UC and CD, respectively. This discrepancy might be explained by the fact that MAdCAM-1 assay measures $α_4β_7$ saturation in circulating T-cells or may be due to a slow onset of action of the drug. The MAdCAM-1 assay is insensitive to dose and should not be used for dose selection. Further studies to evaluate the relative pharmacodynamic contributions of $α_4β_7$ receptor blockade in peripheral blood in distinction to effects on cell-cell interactions in the tissue compartment are a research priority.

In conclusion, a population model characterizing the pharmacokinetic-pharmacodynamic properties of vedolizumab was successfully developed for patients with UC and CD. The modeling results suggested that the typical pharmacokinetics of vedolizumab was similar in patients with UC and those with CD. Albumin and body weight were identified as important predictors of vedolizumab clearance, but the effects of these covariates were only considered clinically meaningful at extreme values. Surprisingly, co-administration of immunosuppressants had no clinically relevant impact on the pharmacokinetics of vedolizumab. However, this finding contrasts with the well-established relationship between prevention of immunogenicity and reduced drug concentrations for TNF-α antagonists. This analysis supports use of fixed dosing with vedolizumab in patients with UC and those with CD.

Example 2

Fecal Calprotectin Assessment

Fecal levels of calprotectin, a neutrophil cytostolic protein, correlate with endoscopic severity of inflammation in inflammatory bowel disease: <50 µg/g: Typical of non-diseased population; >50 to <150 µg/g: Possible mucosal inflammation; >150 µg/g: Active inflammation; Higher levels associated with greater risk of relapse. The aim is to determine if induction treatment with VDZ reduces fecal calprotectin levels in patients with moderately to severely active UC.

Patients from the blinded induction portion of the GEMINI 1 phase 3 clinical trial were tested for fCal in the stool and examined for response or remission relative to calprotectin levels. Stool samples were taken at weeks 0 and 6. fCal levels were measured using the PhiCal calprotectin kit (assay sensitivity of 9 ng/mL of diluted sample).

Figure 14:
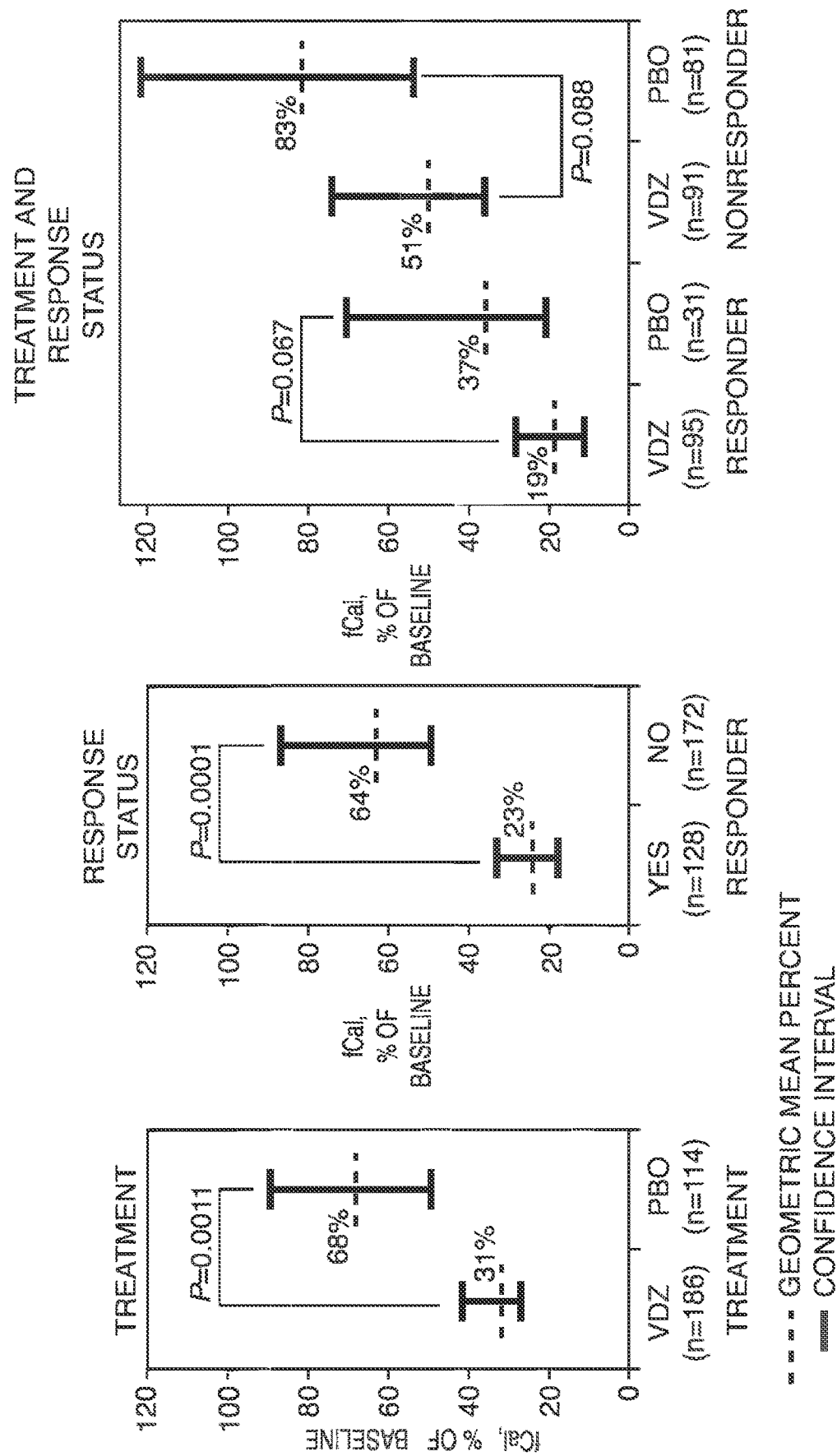
FIG. 14 is Percent of Baseline Calprotectin at Week 6 by Treatment or Response Status.

The Percent of Baseline Calprotectin at Week 6 by Treatment or Response Status is shown in FIG. 14. The P-value is from Wilcoxon rank sum test (2-sided) based on log-transformed data. Only patients with both baseline and week 6 calprotectin values are included in this analysis. A 69% and 32% decrease in geometric mean of fCal was observed for VDZ and PBO-treated patients, respectively (P=0.0011).

TABLE 4

Clinical Response and Remission at Week 6 by Baseline Starting fCal Category

| Baseline Categorical Division | Response, n (%) | | Remission, n (%) | |
|---|---|---|---|---|
| | PBO | VDZ | PBO | VDZ |
| ≤250 µg/g | 8 (29.6) | 20 (54.1) | 2 (7.4) | 7 (18.9) |
| >250 µg/g* | 28 (25) | 82 (46.6) | 6 (5.4) | 29 (16.5) |
| ≤500 µg/g** | 13 (27.7) | 27 (47.4) | 2 (4.3) | 9 (15.8) |
| >500 µg/g | 23 (25.0) | 75 (48.1) | 6 (6.5) | 27 (17.3) |

*Includes >500 µg/g population.
**Includes ≤250 µg/g population.

At baseline, mean fCAL levels were 2370 and 2552 µg/g in PBO and VDZ-treated patients, respectively.

FCAL concentrations declined in patients who responded to induction therapy regardless of treatment. VDZ induction therapy for UC reduced fCal levels at week 6, a marker of mucosal inflammation, significantly more than PBO. Response and remission rates were higher with VDZ regardless of baseline fCal concentration.

Example 3

Deep Remission at Week 6 as Predictor of Clinical Outcome in Ulcerative Colitis

Deep remission, a combination of endoscopic and patient-reported outcomes, is an emerging treatment goal for patients with ulcerative colitis (UC). However, there is currently no standardised definition for assessment of deep remission in UC patients. Statistically significant and clinically meaningful improvement in deep remission endpoints at weeks 6 and 52 were previously reported in the GEMINI 1 population using varying combinations of Mayo subscores of endoscopic and patient-reported outcomes. Here we investigate whether deep remission with VDZ is a predictor of clinical outcomes and health-related quality of life (HRQoL) in patients with UC using post hoc analyses of data from GEMINI 1.

Clinical and HRQoL endpoints were evaluated at week 52 in the maintenance ITT population who were in deep remission at weeks 6 or at 52:

Clinical remission: complete Mayo score of ≤2 points and no individual subscore >1 point Mucosal healing: Mayo endoscopic subscore of ≤1

Corticosteroid (CS)-free remission: patients using oral CS at baseline who have discontinued CS and are in clinical remission at week 52

European Quality of Life-5 Dimension (EQ-5D) visual analogue scale (VAS): increase of ≥7 points represents clinically meaningful improvement.

Inflammatory Bowel Disease Questionnaire (IBDQ) total score: a score >170 is characteristic of the HRQoL of patients in remission. Clinical endpoints were analysed using observed cases at week 52; HRQoL endpoints used the last observation carried forward method to account for missing patients.

TABLE 5

Definitions of Deep Remission based on Mayo endoscopic and patient-reported subscores

| Definition | | Investigator Reported Endoscopic Subscore | Patient Rectal Bleeding Subscore | reported Stool Frequency Subscore |
|---|---|---|---|---|
| 1[a] | Endoscopic remission and symptomatic improvement | 0 | 0 | Decrease or no change |
| 2 | Endoscopic and symptomatic improvement | 0 or 1 | 0 | 0 or 1 |

[a]Definition 1 is considered more stringent than definition 2.

All patients in the maintenance ITT population received 2 doses of VDZ during induction, and rates of deep remission were comparable across treatment groups at week 6 (maintenance baseline) using both definitions. At week 52, almost 3 times as many VDZ-treated patients were in deep remission as were PBO-treated patients, according to either definition.

A greater percentage of patients in deep remission (definition 1 or 2) at week 6 met all clinical endpoints at week 52 compared with those not in deep remission, with VDZ Q4W demonstrating the greatest difference. More patients who were in deep remission at week 6 had improved clinical outcomes with VDZ maintenance treatment than with PBO (FIGS. 15A-15F and 16A-16F). Under definition 1, clinical remission after maintenance treatment with PBO was similar between those in and not in deep remission at week 6. In general, more patients in deep remission (definition 1 or 2) at week 6 reported clinically meaningful improvement in HRQoL at week 52 compared with those not in deep remission. Compared with PBO-treated patients in deep remission, more VDZ-treated patients in deep remission had improved IBDQ and EQ-5D VAS. Even among patients not in deep remission at week 6, maintenance treatment with VDZ resulted in more patients with improved clinical and HRQoL outcomes than those re-randomised to PBO.

Conclusions: A greater percentage of VDZ-treated patients were in deep remission at week 52 using either definition compared with PBO-treated patients; use of the less stringent definition 2 resulted in more patients classified as having achieved deep remission. Using either definition, a greater percentage of patients in deep remission at week 6 met most clinical and HRQoL endpoints at week 52 compared to those not in deep remission. More VDZ-treated patients had improved outcomes than PBO-treated patients. Achievement of deep remission at week 52 aligned with improved clinical and HRQoL outcomes at week 52 regardless of treatment group. These results suggest that monitoring deep remission in future studies could be used to predict patient outcomes.

The invention claimed is:

1. A method of treating a patient suffering from Inflammatory Bowel Disease (IBD), the method comprising
   a) measuring the serum concentration of vedolizumab in a patient, wherein the patient was administered an induction phase dosing regimen of vedolizumab at least two weeks prior,
   b) measuring the concentration of serum albumin in the patient,
   c) measuring the body weight of the patient;
   d) selecting a patient whose measurement of vedolizumab in step a) indicates low clearance, whose measurement of serum albumin in step b) is 3.8 to 5.0 g/dL, and whose body weight is <80 kg; and
   e) administering vedolizumab to the selected patient, thereby treating IBD.

2. The method of claim 1, wherein the patient is selected if the serum concentration of vedolizumab is at least 8 µg per ml.

3. The method of claim 1, further comprising measuring an endoscopic subscore, wherein vedolizumab is continued with an endoscopic subscore of less than 3, less than 2.5, or less than 2.

4. The method of claim 1, further comprising measuring the fecal calprotectin concentration.

5. The method of claim 1, wherein the patient's serum albumin concentration is in the range of 4.0 to 5.0 g/dL.

6. The method of claim 1, wherein the IBD is Crohn's Disease.

7. The method of claim 6, further comprising measuring SES-CD, wherein vedolizumab is continued with a SES-CD score <6, and/or measuring MaRIA, wherein vedolizumab is continued with a MaRIA score <12.

8. A method of treating a patient having Crohn's disease, the method comprising
   a) measuring the serum concentration of vedolizumab in a patient having Crohn's disease, measuring the concentration of serum albumin in the patient, measuring the body weight of the patient, and measuring either SES-CD or MaRIA, wherein the patient was administered an induction phase dosing regimen of vedolizumab at least two weeks prior to the measurements,
   b) selecting a patient whose measurement of vedolizumab in step a) indicates low clearance, whose measurement of serum albumin in step a) is 3.5 to 5.0 g/dL, whose body weight is <80 kg; and whose SES-CD score <6 or MaRIA score <12, and
   c) administering vedolizumab to the selected patient, thereby treating Crohn's disease.

* * * * *

SEQUENCE LISTING

```
<160> NUMBER OF SEQ ID NOS: 11

<210> SEQ ID NO 1
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Gly Ser Gly Tyr Thr Phe
        35                  40                  45

Thr Ser Tyr Trp Met His Trp Val Arg Gln Ala Pro Gly Gln Arg Leu
    50                  55                  60
```

```
Glu Trp Ile Gly Glu Ile Asp Pro Ser Glu Ser Asn Thr Asn Tyr Asn
65                  70                  75                  80

Gln Lys Phe Lys Gly Arg Val Thr Leu Thr Val Asp Ile Ser Ala Ser
            85                  90                  95

Thr Ala Tyr Met Glu Leu Ser Ser Leu Arg Ser Glu Asp Thr Ala Val
                100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Ala Gly Ala Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465                 470
```

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Ala Lys Ser Tyr Gly Asn Thr Tyr Leu Ser Trp Tyr Leu Gln Lys Pro
    50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 3
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60
```

-continued

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Gly
                 85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Trp Met His
1               5
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ile Asp Pro Ser Glu Ser Asn Thr Asn Tyr Asn Gln Lys Phe Lys
1               5                   10                  15

Gly
```

```
<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Tyr Asp Gly Trp Asp Tyr Ala Ile Asp Tyr
1               5                   10
```

```
<210> SEQ ID NO 7
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Arg Ser Ser Gln Ser Leu Ala Lys Ser Tyr Gly Asn Thr Tyr Leu Ser
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Gln Gly Thr His Gln Pro Tyr Thr
1               5

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Lys Val Glu Ile Lys
            100                 105                 110

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
            115
```